United States Patent
Bergman et al.

(10) Patent No.: US 11,045,409 B2
(45) Date of Patent: Jun. 29, 2021

(54) COMPOSITION COMPRISING A WATER-INSOLUBLE SOLID ORGANIC UV-SCREENING AGENT AND A COMPOUND CAPABLE OF ESTABLISHING HYDROGEN BONDS

(71) Applicant: L'OREAL, Paris (FR)

(72) Inventors: Sheba Bergman, Paris (FR); Sandrine Chodorowski-Kimmes, Senlis (FR)

(73) Assignee: L'OREAL, Paris (FR)

(*) Notice: Subject to any disclaimer, the term of this patent is extended or adjusted under 35 U.S.C. 154(b) by 1092 days.

(21) Appl. No.: 14/904,199

(22) PCT Filed: Jun. 23, 2014

(86) PCT No.: PCT/EP2014/063187
§ 371 (c)(1),
(2) Date: Jan. 11, 2016

(87) PCT Pub. No.: WO2015/003893
PCT Pub. Date: Jan. 15, 2015

(65) Prior Publication Data
US 2016/0151267 A1 Jun. 2, 2016

(30) Foreign Application Priority Data
Jul. 12, 2013 (FR) ........................ 1356866

(51) Int. Cl.
| | | |
|---|---|---|
| *A61Q 1/06* | (2006.01) | |
| *A61Q 3/00* | (2006.01) | |
| *A61Q 5/00* | (2006.01) | |
| *A61Q 17/04* | (2006.01) | |
| *A61K 8/49* | (2006.01) | |
| *A61K 8/35* | (2006.01) | |
| *A61K 8/41* | (2006.01) | |
| *A61K 8/58* | (2006.01) | |

(52) U.S. Cl.
CPC .............. *A61K 8/4953* (2013.01); *A61K 8/35* (2013.01); *A61K 8/41* (2013.01); *A61K 8/496* (2013.01); *A61K 8/4966* (2013.01); *A61K 8/585* (2013.01); *A61Q 1/06* (2013.01); *A61Q 17/04* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 2006/0008430 A1* | 1/2006 | Candau | A61K 8/35 424/59 |
| 2010/0028277 A1* | 2/2010 | Chodorowski-Kimmes | A61K 8/4953 424/59 |
| 2010/0330018 A1* | 12/2010 | Lorant | A61K 8/025 424/70.9 |
| 2013/0195778 A1* | 8/2013 | Chodorowski-Kimmes | A61K 8/8194 424/59 |

FOREIGN PATENT DOCUMENTS

EP   2140858 A1   1/2010

* cited by examiner

*Primary Examiner* — Jyothsna A Venkat
(74) *Attorney, Agent, or Firm* — Polsinelli PC

(57) ABSTRACT

The present invention relates to a composition comprising, in a cosmetically acceptable medium, at least one water-insoluble solid organic UV-screening agent (A) at least one compound (B) that may be obtained by reaction between: an oil bearing at least one nucleophilic and/or electrophilic reactive function, and a junction group capable of establishing hydrogen bonds with one or more partner junction groups, each junction group pairing involving at least 3 hydrogen bonds, the said junction group bearing at least one reactive function capable of reacting with the reactive function borne by the oil, the said junction group also comprising at least one unit of formula (I) or (II): in which: R1 and R3, which may be identical or different, represent a divalent carbon-based radical; R2 represents a hydrogen atom or a linear, branched or cyclic, saturated or unsaturated, optionally aromatic, C1-C32 carbon-based and especially hydrocarbon-based radical, which may comprise one or more heteroatoms chosen from O, N, S, F, Si and P.

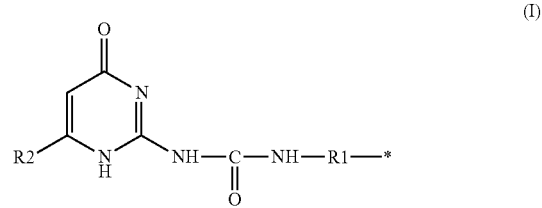

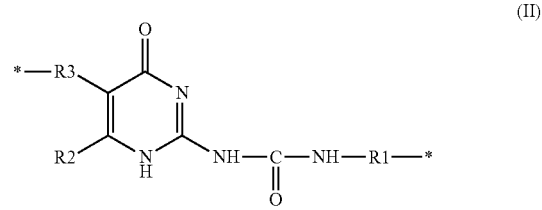

14 Claims, No Drawings

COMPOSITION COMPRISING A WATER-INSOLUBLE SOLID ORGANIC UV-SCREENING AGENT AND A COMPOUND CAPABLE OF ESTABLISHING HYDROGEN BONDS

CROSS REFERENCE TO RELATED APPLICATIONS

This application is a National Phase filing under 35 U.S.C. § 371 of PCT/EP2014/063187 filed on Jun. 23, 2014; and this application claims priority to Application No. 1356866 filed in France on Jul. 12, 2013 under 35 U.S.C. § 119. The entire contents of each application are hereby incorporated by reference.

The present invention relates to a composition comprising, in a cosmetically acceptable medium,
a) at least one water-insoluble solid organic UV-screening agent (A) and
b) at least one compound (B) that may be obtained by reaction between:
an oil bearing at least one nucleophilic and/or electrophilic reactive function, and
a junction group capable of establishing hydrogen bonds with one or more partner junction groups, each junction group pairing involving at least 3 hydrogen bonds, the said junction group bearing at least one reactive function capable of reacting with the reactive function borne by the oil, the said junction group also comprising at least one unit of formula (I) or (II) as defined hereinbelow.

The said compounds (B) make it possible efficiently to dissolve the organic screening agent (A), to obtain uniform distribution of the UV-screening agent (A) on keratin materials, improved water resistance of the UV-screening agent (A), a non-tacky feel of the compound (A)/compound (B) mixture after drying, with improved gloss relative to compound (B) alone, a "long-lasting" effect of a deposit formed on the said keratin materials, the said "long-lasting" effect possibly being linked to the gloss persistence, the persistence per se, optionally combined with a "non-tacky" and/or non-migrating and/or "transfer-resistance" effect.

It is known that light radiation with wavelengths of between 280 nm and 400 nm permits tanning of the human epidermis and that rays with wavelengths more particularly between 280 nm and 320 nm, known as UV-B rays, cause skin burns and erythema which can harm the development of a natural tan. For these reasons, as well as for aesthetic reasons, there is constant demand for means of controlling this natural tanning in order thus to control the colour of the skin; this UV-B radiation should thus be screened out.

It is also known that UV-A rays, with wavelengths between 320 and 400 nm, which cause tanning of the skin, are liable to induce adverse changes therein, in particular in the case of sensitive skin or skin that is continually exposed to solar radiation. UV-A rays cause in particular a loss of elasticity of the skin and the appearance of wrinkles leading to premature ageing of the skin. Thus, for aesthetic and cosmetic reasons, for instance conservation of the skin's natural elasticity, more and more people wish to control the effect of UV-A rays on their skin. It is thus desirable also to screen out UV-A radiation.

With the aim of providing protection of the skin and keratin materials against UV radiation, use is generally made of antisun compositions comprising organic screening agents which are active in the UV-A region and active in the UV-B region. The majority of these screening agents are soluble in water or in the solvents usually used in antisun formulations. Makeup products such as lipsticks, lip glosses and foundations that afford daily protection to the skin and keratin materials against UV radiation by incorporating screening agents into these formulations are now sought. However, the sunscreens commonly used at the so present time are not always compatible with formulations of makeup type, in particular lipsticks, especially compositions containing volatile solvents such as hydrocarbon-based oils containing from 8 to 16 carbon atoms, and especially $C_8$-$C_{16}$ branched alkanes such as $C_8$-$C_{16}$ isoalkanes of petroleum origin (also known as isoparaffins), for instance isododecane (also known as 2,2,4,4,6-pentamethylheptane), isodecane, isohexadecane. This most particularly concerns water-insoluble solid screening agents.

There is still a need to find good solvents for water-insoluble solid sunscreens that are compatible with cosmetic formulations, in particular makeup formulations, and which can improve the cosmetic properties such as the feel, the water resistance, or the absence of staining of clothing. The incorporation of water-insoluble solid screening agents into a cosmetic formulation should also not impair the desired gloss of the deposit in certain applications. This is most particularly true for a use as a lipstick.

It is known practice to incorporate UVA/UVB screening agents into makeup compositions of lipstick and lip gloss type, as recommended in patent US 2010/047 300.

In patent application US 2011/020 251, certain screening agents were proposed for gloss enhancement.

Patent applications US 2010/0 158 834 and WO 2010 080 482 disclose makeup formulations that may contain UV-screening agents, and comprising silicone oils for enhancing the gloss.

Patent applications WO 01/0014352 A2 and US 2004/180 011 teach that phenylated silicone oils can increase the gloss in lipsticks and can increase the UV absorption of the formulation.

It is known from patent applications WO 2010/014 352 and EP 2 303 224 that silicone oils formulated with sunscreens can improve the absorption of UV rays, i.e. the photoprotective efficacy of screening agents.

Patent applications DE 692 17 591, EP 0 528 380, JP 3229383, JP 5194543, KR100205133 and U.S. Pat. No. 5,225,583 teach that alkylaryl 1,3-propanedione silicone derivatives are oils that have moreover the capacity for efficiently absorbing UVA rays. Silicone oils modified with a dibenzoylmethane group absorbing UVA radiation have been proposed in patent application JP 05247063.

Silicone oils modified with a cinnamic acid group absorbing UVB radiation have been proposed in patent application JP 07223932.

Patent application JP 07017983 has proposed silicone oils modified with a 5-allylpentadiene acidic group, and patent application JP 07017982 has proposed silicone oils modified with a 3-naphthylpropenoate group, these groups having UV-radiation-screening properties.

Silicone resins have also been proposed in antisun formulations for increasing the so sun protection factor (SPF) in patent applications AU 2005/330 699, CA 2 604 906, CN 101316577, EP 1 874 266, IN 01680MN2007, IN 247233, JP 2008/537 952, KR 2007/0 121 059, MX 2007/012 730, NZ 562 426, SG 161 269, US 2005/249 690, U.S. Pat. No. 7,887,785 and WO 06/112 865.

Oil-in-silicone emulsions have also been proposed in patent applications US 2005/142 079, US 2009/311 208 and WO 05/065 136 for increasing the sun protection factor (SPF).

It has already been proposed in patent applications FR 2 933 295 and US 2010/0 028 277 to use in cosmetic formulations oils functionalized with ureidopyrimidone derivatives for affording film-forming properties, gloss, persistence, migration resistance and transfer resistance.

The aim of the present invention is to find efficient solvents for water-insoluble solid organic UV-screening agents that can be incorporated into a wide range of cosmetic formulations and especially formulations intended for making up keratin materials, the said solvents making it possible simultaneously to obtain good dissolution of the said UV-screening agents, good photoprotective efficacy, good water resistance, a uniform film-forming deposit of the said UV-screening agents on the keratin materials and persistence of the composition, while at the same time not being tacky and being particularly comfortable to wear, without impairing the gloss and the gloss persistence.

The Applicant has now discovered, surprisingly, that this objective can be achieved by combining particular water-insoluble solid organic UV-screening agents defined below with particular compounds that are capable of establishing hydrogen bonds with particular partner junction groups.

This discovery forms the basis of the present invention.

One subject of the present invention is thus a composition comprising, in a cosmetically acceptable medium:
  a) at least one water-insoluble solid organic UV-screening agent (A) and
  b) at least one compound (B) that may be obtained by reaction between:
an oil bearing at least one nucleophilic and/or electrophilic reactive function, and a junction group capable of establishing hydrogen bonds with one or more partner junction groups, each junction group pairing involving at least 3 hydrogen bonds, the said junction group bearing at least one reactive function capable of reacting with the reactive function borne by the oil, the said junction group also comprising at least one unit of formula (I) or (II) as defined hereinbelow.

The said compounds (B) make it possible efficiently to dissolve the water-insoluble solid organic screening agents (A), to obtain uniform distribution of the said UV-screening agents on keratin materials, good water resistance, a non-tacky feel after drying, a "long-lasting" effect of a deposit formed on the said keratin materials, the said "long-lasting" effect possibly being linked to the gloss persistence, the persistence per se, optionally combined with a "non-tacky" and/or non-migrating and/or "transfer-resistance" effect.

The cosmetic compositions according to the invention moreover show good applicability and good coverage, good adherence to the support, whether it is to the nails, the eyelashes, the skin, the hair or the lips; adequate flexibility and strength of the film, and also excellent gloss durability. The comfort and glidance properties are also very satisfactory.

The present invention also relates to a cosmetic process for treating keratin materials, especially bodily or facial skin, the lips, the nails and/or the eyelashes or the hair, comprising the application to the said materials of a cosmetic composition as defined previously.

The present invention also relates to a process for making up and/or caring for keratin materials, especially bodily or facial skin, the lips, the nails and/or the eyelashes or the hair, comprising the application to the said materials of a cosmetic composition as defined previously.

The present invention also relates to the use of at least one compound (B) as solvent for a solid water-insoluble organic UV-screening agent (A).

The present invention also relates to the use of a composition as defined previously in a product for caring for and/or making up keratin materials, especially bodily or facial skin, the lips, the nails, and/or the eyelashes or the hair, as a gloss agent.

Other characteristics, aspects and advantages of the invention will emerge on reading the detailed description that follows.

The term "cosmetically acceptable" means compatible with the skin and/or its integuments, which has a pleasant colour, odour and feel, and which does not cause any unacceptable discomfort (stinging, tautness or redness) liable to put the consumer off using this composition.

The term "water-insoluble solid organic UV-screening agent (A)" means a solid organic UV-screening agent with a solubility in water of less than 0.1% (0.1 g per 100 g of water) at 25° C. and at an atmospheric pressure of 760 mmHg and having a solubility of at least 1% in isopropyl N-lauroyl sarcosinate, such as the product sold under the trade name Eldew SL205® from Ajinomoto at 25° C. and at an atmospheric pressure of 760 mmHg (at least 1 g in 100 ml of isopropyl N-lauroyl sarcosinate).

The term "solid organic UV-screening agent" means any organic UV-screening agent that is in solid form at room temperature (25° C.) and at atmospheric pressure (1 atmosphere: 760 mmHg).

The term "keratin materials" means human keratin materials such as the skin, the hair, the nails, the eyelashes, the eyebrows, the scalp or mucous membranes, in particular the lips.

The term "gloss agent" means any compound or any mixture of compounds (composition) that is capable of giving gloss and/or of reinforcing gloss on the surface of a human keratin material.

Compounds (B)

The compounds (B) according to the invention may be obtained by reaction between:
  on the one hand, at least one oil bearing at least one nucleophilic and/or electrophilic reactive function, and
  on the other hand, at least one junction group capable of establishing hydrogen bonds with one or more partner junction groups, each junction group pairing involving at least 3 hydrogen bonds, the said junction group bearing at least one reactive function capable of reacting with the reactive function borne by the oil, the said junction group comprising at least one unit of formula (I) or (II) as defined hereinbelow.

Preferably, the compounds (B) according to the invention may be obtained by reaction between:
  on the one hand, at least one oil bearing at least one nucleophilic reactive function chosen from OH and $NH_2$, and
  on the other hand, at least one junction group capable of establishing hydrogen bonds with one or more partner junction groups, each junction group pairing involving at least 3 hydrogen bonds, the said junction group bearing at least one isocyanate or imidazole reactive function, the said junction group comprising at least one unit of formula (I) or (II) as defined hereinbelow.

In conclusion, the compounds (B) according to the invention thus comprise at least one part (HB) originating from the oil and at least one part (G) originating from the junction group, the said part (G) comprising at least one unit of formula (I) or (II).

In particular, the said parts (HB) and (G) are connected via a covalent bond and may especially be connected via a covalent bond formed during the reaction between the OH and/or NH$_2$ reactive functions borne by the oil and the isocyanate functions borne by the junction group; or alternatively between the NH$_2$ reactive functions borne by the oil and the isocyanate or imidazole functions borne by the junction group.

The preferential production of the compounds according to the invention may thus especially be represented schematically by the chemical reaction between the following species:
(HB)-(OH)$_m$(NH$_2$)$_n$+(G)-(NCO)$_p$ or
(HB)-(OH)$_m$(NH$_2$)$_n$+(G)-(imidazole)$_p$ with m, n and p being non-zero integers.

The oil that may be used to prepare compound (B) according to the invention, which may preferably be represented schematically as (HB)-(OH)$_m$(NH$_2$)$_n$, is a fatty substance or a mixture of fatty substances, which is not crystalline at 25° C., and is liquid at room temperature and at atmospheric pressure (25° C., 1 atmosphere); preferably apolar or even, preferably, water-insoluble.

The term "liquid" means that the viscosity of the compound is less than or equal to 2500 centipoises, at 110° C. and 1 atmosphere, measured with a Brookfield DV-I or Brookfield Cap 1000+ rheometer, a person skilled in the art selecting the machine that is suited to the viscosity measurement.

The term "apolar" means a compound whose HLB value (hydrophilic/lipophilic balance) is low; especially less than or equal to 8, preferably less than or equal to 4 and better still less than or equal to 2; preferentially, the HLB value should be low enough to make it possible to obtain a supramolecular material that is not hygroscopic, or not too hygroscopic.

The term "water-insoluble oil" means that the oil fraction that can dissolve in water, at 25° C. and 1 atmosphere, is less than 5% by weight (i.e. 5 g of oil in 100 ml of water); preferably less than 3%.

The term "fatty substance" means especially, but not exclusively, a hydrocarbon-based compound comprising at least one saturated or unsaturated, linear, cyclic or branched alkyl chain, containing at least 6 carbon atoms and possibly comprising polar groups such as an acid, hydroxyl or polyol, amine, amide, phosphoric acid, phosphate, ester, ether, urea, carbamate, thiol, thioether or thioester group, the said chains possibly containing preferably up to 50 carbon atoms.

Preferably, the oil that may be used to prepare the compound according to the invention is a glossy oil, i.e. an oil with a refractive index of greater than or equal to 1.46 at 25° C. and in particular between 1.46 and 1.55 (the refractive index being defined relative to the sodium D line, at 25° C.).

Preferably, the oil that may be used to prepare the compound according to the invention is a non-volatile oil. The term "non-volatile oil" means an oil that is capable of remaining on keratin materials at room temperature and atmospheric pressure for at least several hours, and that especially has a vapour pressure of less than $10^{-3}$ mmHg (0.13 Pa).

Preferably, the oil has a molar mass (Mw) of between 150 and 6000, especially between 170 and 4000, or even between 180 and 2000, preferentially between 200 and 1500 and better still between 220 and 800 g/mol.

The oil that may be used in the context of the present invention bears at least one reactive function capable of reacting with the reactive function borne on the junction group, and is especially capable of reacting chemically with the isocyanate or imidazole groups borne by the junction group; preferably, this function is an OH or NH$_2$ function. Preferably, the oil comprises only OH functions, in particular 1 to 3 OH functions, preferentially primary or secondary OH functions, and better still only primary functions.

The oil according to the present invention is preferably a carbon-based and especially a hydrocarbon-based oil, which, besides the reactive function capable of reacting with the junction group, may comprise oxygen, nitrogen, sulfur and/or phosphorus atoms. The oil is very preferentially chosen from cosmetically acceptable oils.

The oil that may be used, alone or as a mixture, in the context of the present invention may be chosen from:
(i) saturated or unsaturated, linear, branched or cyclic fatty alcohols preferably comprising from 6 to 50 carbon atoms, comprising 1 or more OH; optionally comprising one or more NH$_2$.

Mention may be made in particular of:
saturated or unsaturated, linear or branched C$_6$-C$_{50}$, especially C$_6$-C$_{32}$ and in particular C$_8$-C$_{28}$ monoalcohols, and especially isostearyl alcohol, cetyl alcohol, oleic alcohol, oleyl alcohol, isopalmitoyl alcohol, 2-butyloctanol, 2-hexyldecanol, 2-octyldecanol, 2-octyldodecanol, 2-octyltetradecanol, 2-decyltetradecanol and 2-dodecylhexadecanol, and especially the alcohols sold under the name Jarcol by the company Jarchem Industries, such as Jarcol I-12, Jarcol I-16, Jarcol I-20 and Jarcol I-24; linear or branched C$_8$-C$_{28}$ monoalcohols are preferred;

linear or branched, saturated or unsaturated C$_6$-C$_{50}$, especially C$_6$-C$_{40}$ and in particular C$_8$-C$_{38}$ diols, especially branched C$_{32}$-C$_{36}$ diols, and in particular the commercial product Pripol 2033 from Uniqema;

linear or branched, saturated or unsaturated C$_6$-C$_{50}$, especially C$_6$-C$_{32}$ and in particular C$_8$-C$_{28}$ triols, and especially phytanetriol;

(ii) esters bearing at least one free OH group, and especially partial polyol esters and ethers, and hydroxylated carboxylic acid esters.

The term "partial polyol ester" means esters prepared by esterification of a polyol with a substituted or unsubstituted carboxylic acid, the reaction not being total, i.e. not performed on all of the free OHs of the polyol; as a result, the ester thus still comprises at least one free OH.

Preferably, the carboxylic acid is a monoacid. A mixture of carboxylic acids, especially monocarboxylic acids, may also be used.

The term "hydroxylated carboxylic acid ester" means (mono and poly) esters prepared by reaction between a carboxylic acid bearing at least one OH function, and one or more (mono or poly)alcohols, preferably a monoalcohol, the reaction possibly being total or partial (performed on all or some of the free OHs of the alcohol).

Among the polyols that may be used for preparing the above esters are polyols containing from 2 to 38 carbon atoms and preferably containing from 3 to 8 carbons.

Polyols that may be mentioned include propylene glycol, glycerol, neopentyl glycol, trimethylolpropane, trimethylolethane, polyglycerols and especially polyglycerol-2, polyglycerol-3 and polyglycerol-10; erythritol, dipentaerythritol, pentaerythritol, bis(trimethylolpropane), phytanetriol, sucrose, glucose, methylglucose, sorbitol, fructose, xylose, mannitol or glucosamine; and also diol dimers obtained especially from fatty acid dimers, especially branched aliphatic and/or alicyclic C$_{32}$-C$_{38}$ and especially C$_{36}$ diols, such as those defined in the article Hofer et al., European Coating Journal (March 2000), pages 26-37; and mixtures thereof.

According to one embodiment of the invention, use may be made of partial esters of $C_2$-$C_{38}$ polyols and of $C_6$-$C_{50}$ monocarboxylic acids.

According to another embodiment of the invention, use may be made of partial esters of $C_2$-$C_{38}$ polyols and of $C_3$-$C_{12}$ dicarboxylic acids.

According to another embodiment of the invention, use may be made of esters of $C_3$-$C_{50}$ monoalcohols and of hydroxylated $C_4$-$C_{28}$ mono-, di- or tricarboxylic acids, and preferably esters of monoalcohols, preferably $C_8$-$C_{20}$ monoalcohols, and of hydroxylated $C_4$-$C_{10}$ mono-, di- or tricarboxylic acids.

Among the monoalcohols that may be used for preparing the esters, mention may be made of linear or branched, preferably branched, $C_3$-$C_{50}$ and preferably $C_8$-$C_{20}$ monoalcohols, and especially 2-ethylhexanol, octanol, isostearyl alcohol and 2-octyldodecanol, and mixtures thereof.

Monoacids containing 6 to 50 carbon atoms that may be mentioned include octyldodecylic acid, hexyldecylic acid, ethylhexylic acid, isostearic acid, nonanoic acid, isononanoic acid, arachidic acid, stearic acid, palmitic acid, oleic acid, oxalic acid, capric acid, decylic acid and decanoic acid.

As diacids containing 3 to 12 carbon atoms, which are in particular linear or branched, and saturated or unsaturated, mention may be made of adipic acid, succinic acid, fumaric acid, oxalic acid, hexanedioic acid and maleic acid; and mixtures thereof.

Among the hydroxylated mono-, di- or tricarboxylic acids, mention may be made of monohydroxylated or polyhydroxylated acids, preferably monohydroxylated acids, containing, for example, 4 to 28 carbon atoms, and especially 12-hydroxystearic acid, ricinoleic acid, malic acid, lactic acid and citric acid; and mixtures thereof.

Thus, the oil that may be used, alone or as a mixture, in the present invention may be chosen, alone or as a mixture, from:

pentaerythritol partial esters, and especially pentaerythrityl adipate, pentaerythrityl caprate, pentaerythrityl succinate, pentaerythrityl tetraisononanoate, pentaerythrityl triisononanoate, pentaerythrityl tetraisostearate, pentaerythrityl triisostearate, pentaerythrityl 2-(tetradecyl)tetradecanoate, pentaerythrityl (tetraethyl) hexanoate and pentaerythrityl (tetraoctyl)dodecanoate;

dipentaerythritol diesters, triesters, tetraesters or pentaesters, and especially dipentaerythrityl pentaisononanoate, dipentaerythrityl pentaisostearate, dipentaerythrityl tetra isostearate and dipentaerythrityl tris (polyhydroxystearate);

trimethylolpropane monoesters and diesters, for instance trimethylolpropane monoisostearate, trimethylolpropane diisostearate, trimethylolpropane mono-2-ethylhexanoate and trimethylolpropane bis(2-ethylhexanoate);

bis(trimethylolpropane) monoesters, diesters and triesters, for instance bis(trimethylolpropane) diisostearate, bis(trimethylolpropane) triisostearate and bis(trimethylolpropane) triethylhexanoate;

partial monoesters or polyesters of glycerol or of polyglycerols, and especially:

glyceryl diisostearate and glyceryl diisononanoate;

polyglycerol-2 monoesters, diesters and triesters; for example with isostearic acid, 2-ethylhexanoic acid and/or isononanoic acid; and especially polyglyceryl-2 isostearate; polyglyceryl-2 diisostearate; polyglyceryl-2 triisostearate; polyglyceryl-2 nonaisostearate; polyglyceryl-2 nonanoate;

polyglycerol-3 monoesters, diesters, triesters or tetraesters; for example with either isostearic acid, 2-ethylhexanoic acid and/or isononanoic acid; and especially polyglyceryl-3 isostearate; polyglyceryl-3 diisostearate; polyglyceryl-3 triisostearate; polyglyceryl-3 nonaisostearate; polyglyceryl-3 nonanoate;

polyglycerol-10 partial esters and in particular polyglyceryl-10 nonaisostearate; polyglyceryl-10 nonanoate; polyglyceryl-10 isostearate; polyglyceryl-10 diisostearate; polyglyceryl-10 triisostearate;

propylene glycol monoesters, for instance propylene glycol monoisostearate, propylene glycol neopentanoate or propylene glycol monooctanoate;

diol dimer monoesters, for instance isostearyl dimer dilinoleate and octyldodecyl dimer dilinoleate;

esters between a hydroxylated monocarboxylic, dicarboxylic or tricarboxylic acid and monoalcohols, and in particular:

esters, especially monoesters, of 12-hydroxystearic acid; such as octyl hydroxystearate and 2-octyldodecyl hydroxystearate; mention may also be made of the corresponding oligomeric polyhydroxystearates, especially with a degree of polymerization of from 1 to 10, containing at least one residual OH;

lactic acid esters, especially C4-40 alkyl lactates, such as 2-ethylhexyl lactate, diisostearyl lactate, isostearyl lactate, isononyl lactate and 2-octyldodecyl lactate;

malic acid esters, and especially C4-40 alkyl malates, such as bis(2-ethyl)hexyl malate, diisostearyl malate and bis(2-octyl)dodecyl malate;

citric acid esters, and especially C4-40 alkyl citrates, such as triisostearyl citrate, triisocetyl citrate and triisoarachidyl citrate;

Preference will be given more particularly to malic acid esters, and especially $C_4$-$C_{40}$ and preferably $C_8$-$C_{22}$ alkyl malates, such as 2-diethylhexyl malate, diisostearyl malate and 2-dioctyldodecyl malate.

(iii) natural or modified natural or plant hydroxylated oils

Mention may be made especially of:

triglyceryl esters bearing one or more OHs;

hydrogenated or non-hydrogenated castor oil,—modified epoxidized oils, the so modification consisting in opening the epoxy function to obtain a diol, and especially hydroxylated modified soybean oil; hydroxylated soybean oils (directly hydroxylated or epoxidized beforehand); and especially the oils Agrol 2.0, Agrol 3.0 and Agrol 7.0 sold by Bio-Based Technologies, LLC; the oil Soyol R2-052 from the company Urethane Soy System; the Renuva oils sold by Dow Chemical; the oils BioH Polyol 210 and 500 sold by Cargill.

Preferably, the oils that may be used in the present invention are chosen from 2-octyldodecanol, diisostearyl malate, 2-butyloctanol, 2-hexyldecanol, 2-decyltetradecanol; hydrogenated or non-hydrogenated castor oil; hydroxylated modified soybean oil, and mixtures thereof.

More particularly, the oils that may be used in the present invention are chosen from diisostearyl malate, 2-decyltetradecanol and hydrogenated or non-hydrogenated castor oil, and mixtures thereof.

The junction group that may be used to form the compound according to the invention bears at least one reactive group, especially isocyanate or imidazole, capable of reacting with the reactive functions, especially OH and/or $NH_2$ (exclusively $NH_2$ for imidazole), of the oil, in order to form a covalent bond, especially of urethane type, between the said oil and the said junction group.

The said junction group is capable of establishing H bonds with one or more partner junction groups, of identical or different chemical nature, each junction group pairing involving at least 3 H (hydrogen) bonds, preferably at least 4 H bonds and preferentially 4 H bonds.

For the purposes of the invention, the term "junction group" means any functional group comprising groups that are H bond donors or acceptors, and capable of establishing at least three H bonds, preferably at least 4 H bonds, preferentially 4 H bonds, with an identical or different partner junction group.

For the purposes of the invention, the term "partner junction group" means any junction group that can establish H bonds with one or more junction groups of the same or of another polymer according to the invention. The junction groups may be of identical or different chemical nature. If they are identical, they may then establish H bonds between themselves and are then referred to as self-complementary junction groups. If they are different, they are chosen such that they are complementary with respect to H interactions.

The said junction group, bearing isocyanate groups, may thus be represented schematically as (G)-(NCO)$_p$, p being a non-zero integer, preferably equal to 1 or 2.

The junction group moreover comprises at least one monovalent unit of formula (I) and/or at least one divalent unit of formula (II), as defined below:

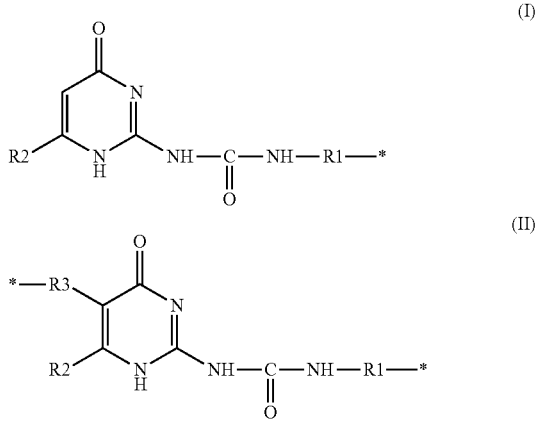

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;
R2 represents a hydrogen atom or a linear, branched or cyclic, saturated or unsaturated, optionally aromatic, $C_1$-$C_{32}$ carbon-based and especially hydrocarbon-based (alkyl) radical, which may comprise one or more heteroatoms chosen from O, N, S, F, Si and P.

The radical R1 may especially be:
a linear or branched, divalent $C_2$-$C_{12}$ alkylene group, especially a 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene) or 1,7-(3,7-dimethyloctylene) group;
a divalent $C_4$-$C_{16}$ cycloalkylene or arylene group, chosen especially from the following radicals: tolylene, 2-methyl-1,3-phenylene, 4-methyl-1,3-phenylene; 4,4'-methylenebiscyclohexylene; 4,4-bisphenylenemethylene; or of structure:

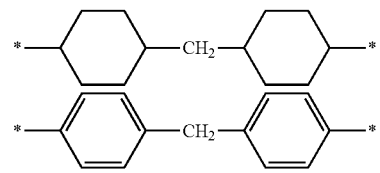

or alternatively the divalent radical Y of structure:

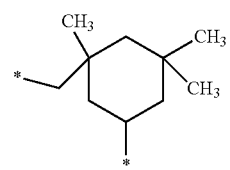 [SMILES: *CC1(C)CC(*)CC(C)(C)C1]

Preferentially, R1 represents Y, —(CH$_2$)$_6$— or 4,4'-methylenebiscyclohexylene.

The radical R2 may especially be H or alternatively:
a $C_1$-$C_{32}$, in particular $C_1$-$C_{16}$ or even $C_1$-$C_{10}$ alkyl group;
a $C_4$-$C_{12}$ cycloalkyl group;
a $C_4$-$C_{12}$ aryl group;
a ($C_4$-$C_{12}$)aryl($C_1$-$C_{18}$)alkyl group;
a $C_1$-$C_4$ alkoxy group;
an arylalkoxy group, in particular an aryl($C_1$-$C_4$)alkoxy group;
a $C_4$-$C_{12}$ heterocycle;
or a combination of these radicals, which may be optionally substituted with an amino, ester and/or hydroxyl function.

Preferably, R2 represents H, CH$_3$, ethyl, $C_{13}H_{27}$, $C_7H_{15}$, phenyl, isopropyl, isobutyl, n-butyl, tert-butyl, n-propyl or —CH(C$_2$H$_5$)(C$_4$H$_9$).

Preferably, R3 represents a divalent radical —R'3—O—C(O)—NH—R'4— in which R'3 and R'4, which may be identical or different, represent a divalent carbon-based radical chosen from a linear or branched $C_1$-$C_{32}$ alkyl group, a $C_4$-$C_{16}$ cycloalkyl group and a $C_4$-$C_{16}$ aryl group; or a mixture thereof.

In particular, R'3 and R'4 may represent methylene, 1,2-ethylene, 1,6-hexylene, 1,4-butylene, 1,6-(2,4,4-trimethylhexylene), 1,4-(4-methylpentylene), 1,5-(5-methylhexylene); 1,6-(6-methylheptylene); 1,5-(2,2,5-trimethylhexylene), 1,7-(3,7-dimethyloctylene); 4,4'-methylenebiscyclohexylene; 2-methyl-1,3-phenylene; 4-methyl-1,3-phenylene; 4,4'-bisphenylenemethylene; 1,2-tolylene, 1,4-tolylene, 2,4-tolylene, 2,6-tolylene; 1,5-naphthylene; tetramethylxylylene; Y.

Most particularly, R'3 may represent a $C_1$-$C_4$ alkylene, especially 1,2-ethylene.

Preferably, R'4 may represent the divalent radical Y.

Most particularly, R3 may have the structure:

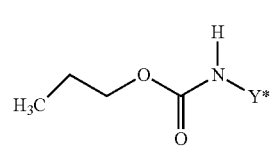

The preferred compounds of formula (I) are chosen from those for which:
R1 is Y and
R2 denotes hydrogen, methyl, ethyl, n-propyl or isobutyl, and preferably hydrogen.

The preferred compounds of formula (II) are chosen from those for which:
R1 is Y and
R2 denotes hydrogen, methyl or ethyl, and preferably hydrogen, and
R3 denotes —R3'—O—CO—NH—R4' and
R3' denotes 1,2-ethylene and
R4' is Y.

In a particularly preferred manner, the following may apply in formula (I):
R1=Y, R2=methyl, which gives the unit of formula:

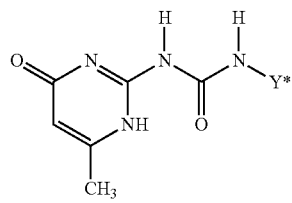

R1=—(CH$_2$)$_6$—, R2=methyl, which gives the unit of formula:

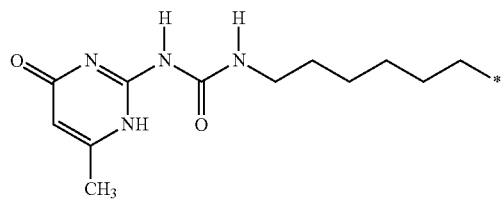

R1=—(CH$_2$)$_6$—, R2=isopropyl, which gives the unit of formula:

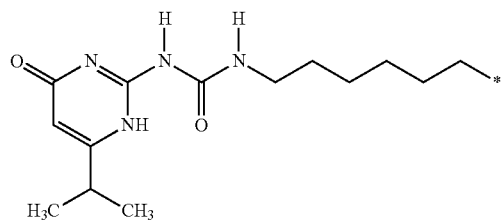

R1=4,4'-methylenebiscyclohexylene and R2=methyl, which gives the unit of formula:

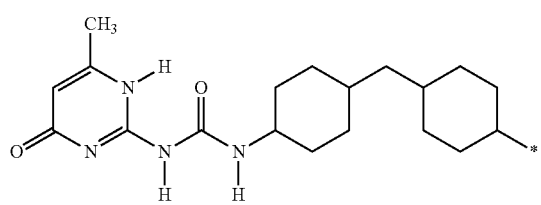

In a particularly preferred manner, in formula (II), R1 represents the radical Y, R2=methyl and R3=—(CH$_2$)$_2$OCO—NH—Y, which gives the divalent unit of formula:

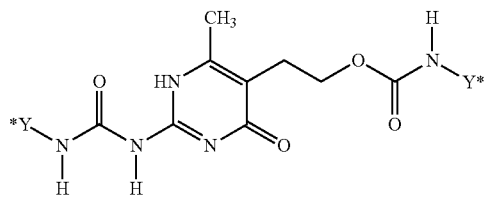

The junction groups bearing only one isocyanate function may have the formula:

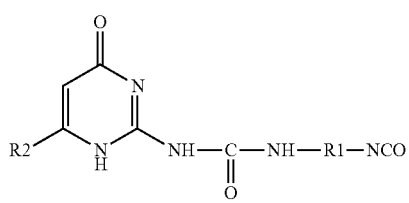

in which R1 and R2 are as defined above; and in particular:
R1 represents Y, —(CH$_2$)$_6$—, CH$_2$CH(CH$_3$)—CH$_2$—C(CH$_3$)$_2$—CH$_2$—CH$_2$, 4,4'-methylenebiscyclohexylene or 2-methyl-1,3-phenylene; and/or
R2 represents H, CH$_3$, ethyl, C$_{13}$H$_{27}$, C$_7$H$_{15}$, phenyl, isopropyl, isobutyl, n-butyl, tert-butyl, n-propyl or —CH(C$_2$H$_5$)(C$_4$H$_9$).

Preferably, the junction groups may be chosen from the following groups:

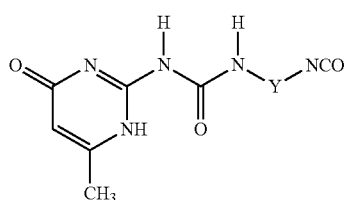

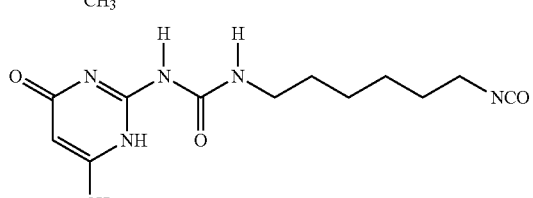

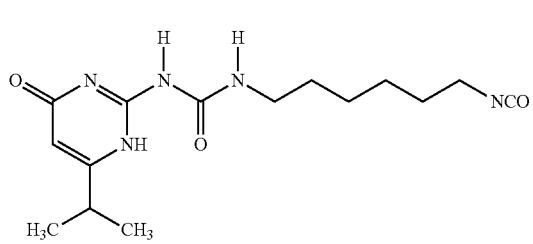

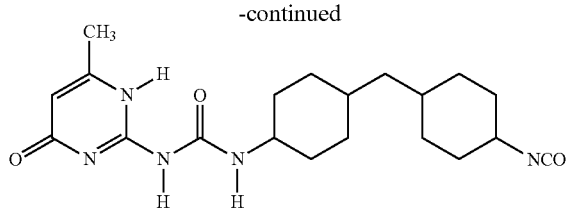

The junction groups bearing two isocyanate functions may have the formula:

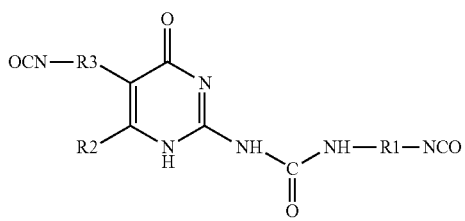

in which R1, R2 and R3 are as defined above, and in particular:

R1 represents Y, —(CH$_2$)$_2$—, —(CH$_2$)$_6$—, —CH$_2$CH(CH$_3$)—CH$_2$—C(CH$_3$)$_2$—CH$_2$—CH$_2$, 4,4'-methylenebiscyclohexylene or 2-methyl-1,3-phenylene; and/or R2 represents H, CH$_3$, ethyl, C$_{13}$H$_{27}$, C$_7$H$_{15}$, phenyl, isopropyl, isobutyl, n-butyl, tert-butyl, n-propyl or —CH(C$_2$H$_5$)(C$_4$H$_9$); and/or R3 represents a divalent radical —R'3-O—C(O)—NH—R'4- in which R'3 and R'4, which may be identical or different, represent a divalent carbon-based radical chosen from a linear or branched C$_1$-C$_{30}$ alkyl group, a C$_4$-C$_{12}$ cycloalkyl group and a C$_4$-C$_{12}$ aryl group; or mixtures thereof; and in particular R'3 represents a C$_1$-C$_4$ alkylene, in particular 1,2-ethylene, and R'4 represents the divalent radical Y.

A junction group that is most particularly preferred is that of formula:

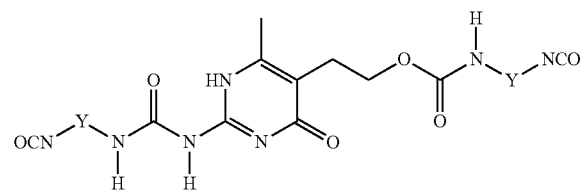

Among the junction groups bearing an imidazole group, mention may be made of the following compound:

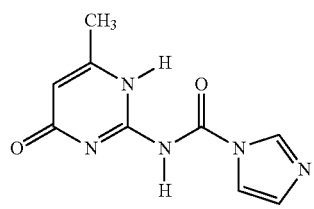 [SMILES: Cc1cc(=O)nc(NC(=O)n2ccnc2)[nH]1]

According to one particular embodiment of the invention, the junction groups may be attached to the oil by functionalization of the junction group with an isocyanate or imidazole.

According to another embodiment, it is possible to perform the reverse reaction by prefunctionalizing the oil with a diisocyanate.

As mentioned above (first mode), the compound according to the invention may thus result from the chemical reaction between an oil (HB)-(OH)$_m$(NH$_2$)$_n$ and a junction group (G)-(NCO)$_p$ or (G)-(imidazole)$_p$.

Preferably, the oil comprises only hydroxyl functions and the junction group comprises 1 or 2 isocyanate functions, which leads to the following reactions:

(HB)-(OH)$_m$+OCN-(G)-NCO→(HB)-OC(O)NH-(G)-NHC(O)-(HB)

(HB)-(OH)$_m$+(G)-NCO→(HB)-OC(O)NH-(G)

with m=integer greater than or equal to 1.

Preferably, the degree of grafting of the free OHs of the oil is between 1% and 100%, especially between 20% and 100% and better still between 50% and 100%; preferably, this degree is 100% (all the free OHs are functionalized with a junction group), especially when the oil initially comprises only one OH function.

The compound according to the invention may be prepared via the processes usually used by those skilled in the art for forming a urethane bond, between the free OH functions of the oil and the isocyanate functions borne by the junction group.

By way of illustration, a general preparation process consists, under a controlled atmosphere and in an anhydrous medium, in:

ensuring that the oil to be functionalized does not comprise any residual water;

heating the oil comprising at least one reactive function, especially OH, to a temperature that may be between 60° C. and 140° C.;

adding the junction group bearing the reactive functions, in particular isocyanate;

optionally stirring the mixture, at a temperature of about 100-140° C.; for 1 to 24 hours;

monitoring by infrared spectroscopy the disappearance of the characteristic band for isocyanates (between 2500 and 2800 cm$^{-1}$) so as to stop the reaction on total disappearance of the peak, and then to allow the final product to cool to room temperature.

The reaction may be performed in the presence of a solvent, especially methyltetrahydrofuran, propylene carbonate, diethyl carbonate, tetrahydrofuran, toluene or butyl acetate; the reaction may also be performed without solvent, in which case the oil may serve as solvent.

It is also possible to add a conventional catalyst for forming a urethane bond. By way of example, mention may be made of dibutyltin dilaurate, tertiary amines such as DBU and DABCO, dioctyltin and dioctylbismuth.

The compound may finally be washed and dried, or even purified, according to the general knowledge of those skilled in the art.

According to the second embodiment (under the same temperature conditions and with the same solvents and catalysts as in the preceding reaction mode), the reaction may comprise the following steps performed under a controlled atmosphere and in an anhydrous medium:

(i) functionalization of the oil with a diisocyanate according to the reaction scheme:

(HB)-OH (1 eq.)+NCO—X—NCO (1 eq.)→(HB)-OC(O)—NH—X—NCO and then
(iia) either reaction with 6-methylisocytosine:
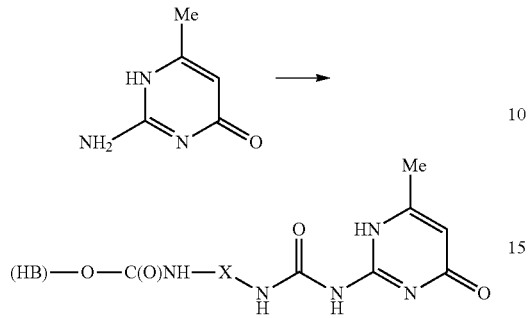
or
(iib) or reaction with 5-hydroxyethyl-6-methylisocytosine:
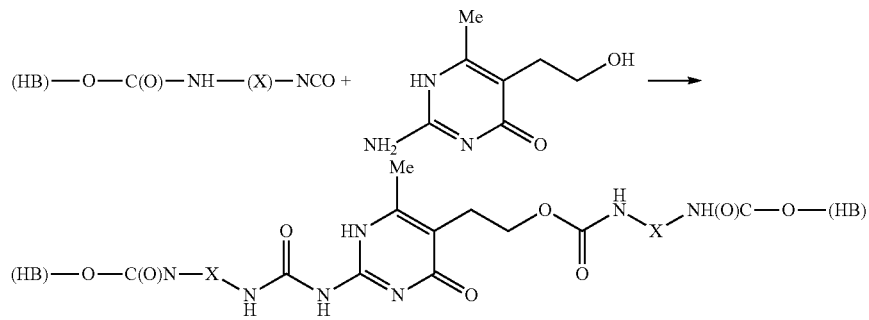
An illustration of such a reaction is given in Folmer et al., Adv. Mater, 12, 874-78 (2000).
Compounds (B) according to the invention may especially correspond to the following structures:
ureidopyrimidone-functionalized octyldodecanol of structure:

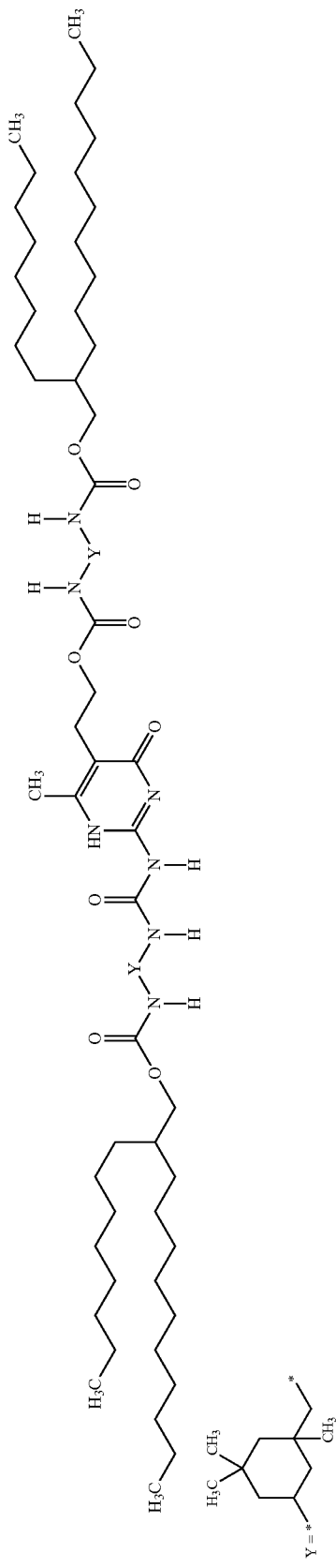

or of structure:
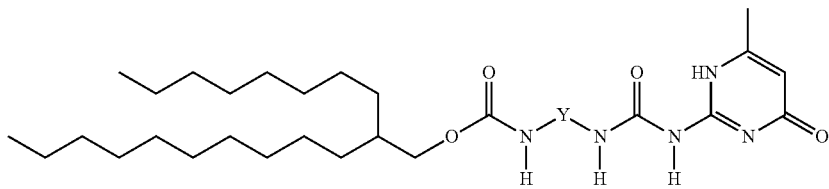
ureidopyrimidone-functionalized diisostearyl malate of structure:
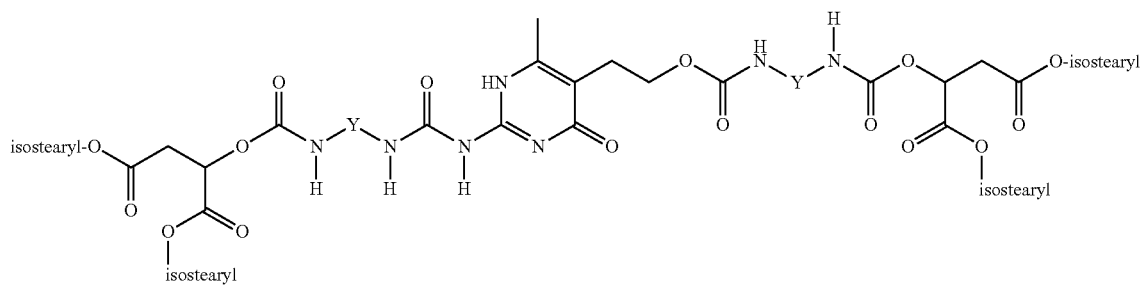
or of structure:
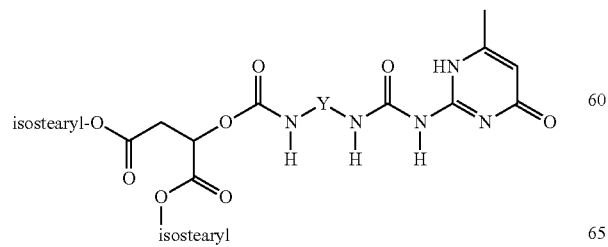

ureidopyrimidone-functionalized castor oil of structure:
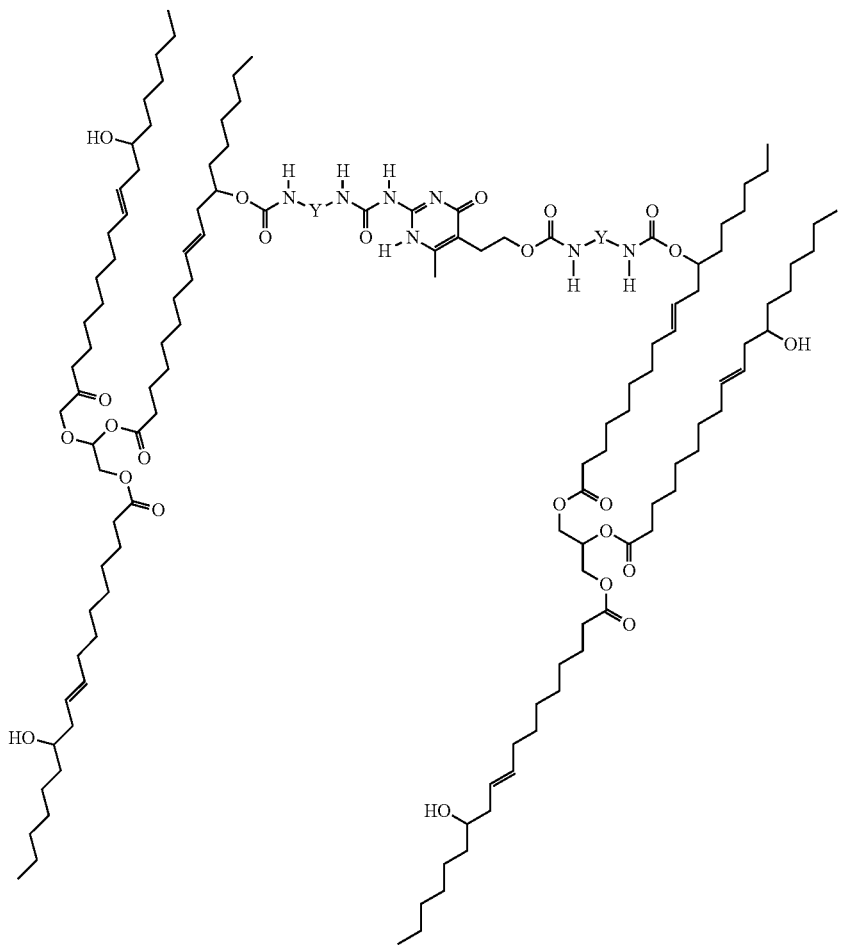
45
or of structure:
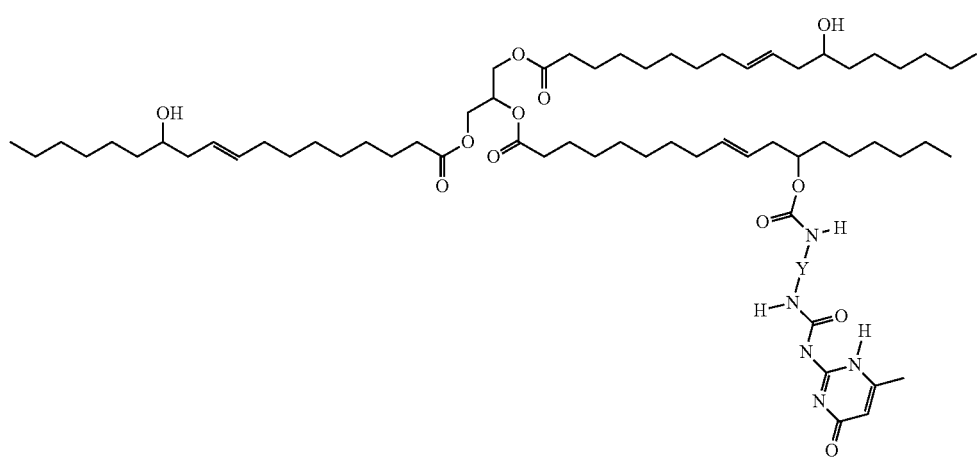

ureidopyrimidone-functionalized 2-hexyldecanol of structure:
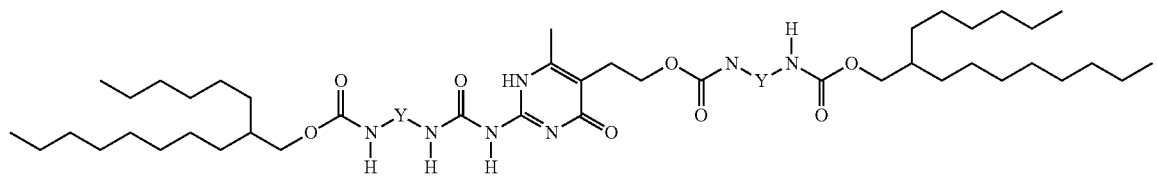
or of structure:
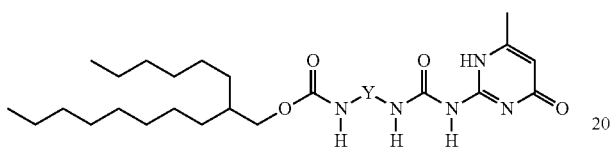
ureidopyrimidone-functionalized 2-decyltetradecanol of structure:
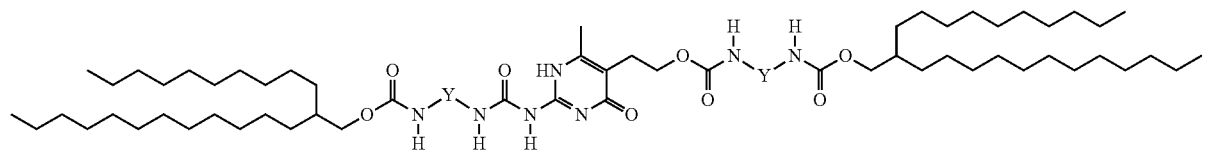
or of structure:
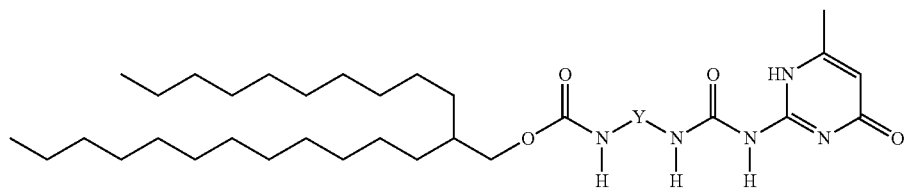
Use will more particularly be made of the following compounds:
ureidopyrimidone-functionalized diisostearyl malate of structure:
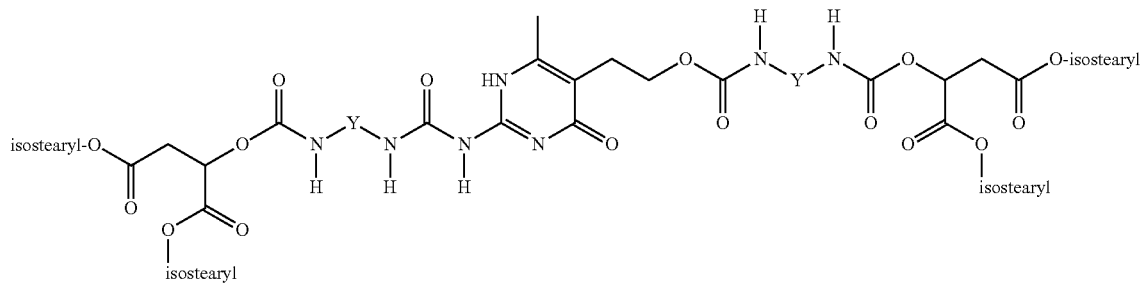

or of structure:

[Chemical structure: isostearyl-O-...-C(=O)-O-...-O-C(=O)-N(H)-Y-N(H)-C(=O)-N(H)-pyrimidone, with isostearyl ester branch]

ureidopyrimidone-functionalized 2-decyltetradecanol of structure:

[Chemical structure showing 2-decyltetradecanol with ureidopyrimidone linkage on both ends]

or of structure:

[Chemical structure showing 2-decyltetradecanol-O-C(=O)-N(H)-Y-N(H)-C(=O)-N(H)-pyrimidone]

Preferably, the compounds according to the invention have a dynamic viscosity ranging from 10 to 1200 Pa·s.

The dynamic viscosity is measured at room temperature (25° C.) according to the following protocol:

A solution containing the oil in accordance with the invention at 50% in isododecane (about 3 ml) is prepared. The solution is deposited on the bottom plate of a Haake RheoStress 600 rheometer with the following characteristics:
measuring body: titanium cone-plate geometry, 60 mm diameter, angle of 2° (ref.: 96012). Evaporation of the isododecane from 3 ml of solution takes place on the lower plate of the measuring body.
cone-plate gap: 100 μm
frequency scan from 0.1 to 50 Hz in logarithmic distribution at room temperature (25° C.) under a shear stress of 1 Pa located in the linear domain of the behaviour.

The isododecane is allowed to evaporate off at room temperature (25° C.) for 5 hours. The sample has a viscous honey appearance.

The storage moduli G' and the loss moduli G" as a function of the frequency f of the oscillatory shear stress are determined using the rheometer. The dynamic viscosity $\eta^*$ as a function of the frequency f is calculated from the storage moduli G' and the loss moduli G" using the following equation:

$$\eta^* = \sqrt{(G'^2 + G''^2)}/\omega \text{ with } \omega = 2\pi f$$

The number-average molecular mass (Mn) of the compound according to the invention is preferably between 180 and 8000, preferably from 200 to 6000, or even from 300 to 4000, better still from 400 to 3000 and preferentially from 500 to 1500.

The amount of compound (B) present in the compositions obviously depends on the type of composition and on the desired properties, and may vary within a very wide range, generally between 1% and 80% by weight, preferably between 2% and 75% by weight and especially between 5% and 50% by weight.

Water-Insoluble Solid Organic UV-Screening Agents (A)

The water-insoluble solid screening agents (A) according to the invention are preferably chosen from:
(i) water-insoluble solid UV-screening agents of the dibenzoylmethane type
(ii) water-insoluble solid UV-screening agents of the triazine type
(iii) water-insoluble solid UV-screening agents of the benzophenone type
(iv) water-insoluble solid UV-screening agents of the merocyanine type
(v) water-insoluble solid UV-screening agents of the benzylidenecamphor type
(vi) water-insoluble solid UV-screening agents of the phenylbenzotriazole type
(vii) water-insoluble solid UV-screening agents of the para-aminobenzoic type and
(viii) mixtures thereof.

Water-Insoluble Solid UV-Screening Agents (A) of the Dibenzoylmethane Type

Among the water-insoluble solid UV-screening agents of the dibenzoylmethane type, mention may be made especially of:
2-methyldibenzoylmethane
4-methyldibenzoylmethane
4-isopropyldibenzoylmethane
4-tert-butyldibenzoylmethane
2,4-dimethyldibenzoylmethane
2,5-dimethyldibenzoylmethane
4,4'-diisopropyldibenzoylmethane
4,4'-dimethoxydibenzoylmethane
4-tert-butyl-4'-methoxydibenzoylmethane
2-methyl-5-isopropyl-4'-methoxydibenzoylmethane
2-methyl-5-tert-butyl-4'-methoxydibenzoylmethane
2,4-dimethyl-4'-methoxydibenzoylmethane
2,6-dimethyl-4-tert-butyl-4'-methoxydibenzoylmethane 1-(4-methoxy-1-benzofuran-5-yl)-3-phenylpropane-1,3-dione (Pongamol).

Among the dibenzoylmethane derivatives mentioned above, use will be made most particularly of 4-(tert-butyl)-4'-methoxydibenzoylmethane or Butylmethoxydibenzoylmethane or avobenzone, sold under the trade name Parsol 1789 by the company DSM Nutritional Products; this screening agent corresponds so to the following formula:

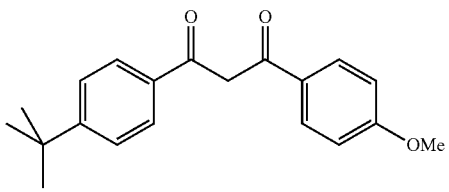 [SMILES: COc1ccc(C(=O)CC(=O)c2ccc(C(C)(C)C)cc2)cc1]

Water-Insoluble Solid UV-Screening Agents (A) of the Triazine Type

The water-insoluble solid UV-screening agents of the triazine type in accordance with the invention are preferably chosen from:
(i) the 1,3,5-triazine derivatives of formula (1) below

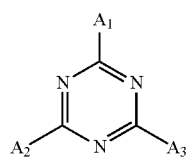
(1)

in which the radicals $A_1$, $A_2$ and $A_3$, which may be identical or different, are chosen from the groups of formula (2):

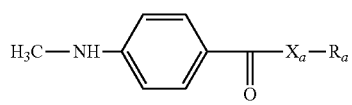
(2)

in which:
$X_a$, which may be identical or different, represent oxygen or an —NH— radical;
$R_a$, which may be identical or different, are chosen from a linear or branched $C_1$-$C_{18}$ alkyl radical; a $C_5$-$C_{12}$ cycloalkyl radical optionally substituted with one or more $C_1$-$C_4$ alkyl radicals; a polyoxyethylene radical comprising from 1 to 6 ethylene oxide units and in which the end OH group is methylated; a radical of formula (3), (4) or (5) below:

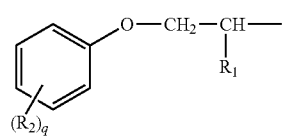
(3)

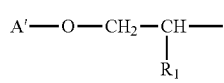
(4)

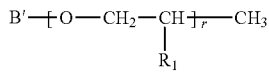
(5)

in which:
$R_1$ is hydrogen or a methyl radical;
$R_2$ is a $C_1$-$C_9$ alkyl radical;
q is an integer ranging from 0 to 3;
r is an integer ranging from 1 to 10;
A' is a $C_4$-$C_8$ alkyl radical or a $C_5$-$C_8$ cycloalkyl radical;
B' is chosen from: a linear or branched $C_1$-$C_8$ alkyl radical; a $C_5$-$C_8$ cycloalkyl radical; an aryl radical optionally substituted with one or more $C_1$-$C_4$ alkyl radicals;
it being understood that when $A_1$, $A_2$ and $A_3$ are identical and $X_a$ denotes an oxygen atom, then $R_a$ represents a branched $C_6$-$C_{18}$ alkyl radical.

A first more particularly preferred family of 1,3,5-triazine derivatives of formula (I) is that described especially in document EP-A-0 517 104, which corresponds to the 1,3,5-triazines of formula (1) in which $A_1$, $A_2$ and $A_3$ are of formula (2) and have the following characteristics:
one of the radicals $X_a$—$R_a$ represents the radical —NH—$R_a$ with $R_a$ chosen from: a $C_5$-$C_{12}$ cycloalkyl radical optionally substituted with one or more $C_1$-$C_4$ alkyl radicals; a radical of formula (3), (4) or (5) above in which:
B' is a $C_1$-$C_4$ alkyl radical;
$R_2$ is a methyl radical;
the other two $X_a$—$R_a$ represent the radical —O—$R_a$ with $R_a$, which may be identical or different, chosen from: hydrogen; an alkali metal; an ammonium radical optionally substituted with one or more alkyl or hydroxyalkyl radicals; a linear or branched $C_1$-$C_{18}$ alkyl radical; a $C_5$-$C_{12}$ cycloalkyl radical optionally substituted with one or more $C_1$-$C_4$ alkyl radicals; a radical of formula (3), (4) or (5) above in which:
B' is a $C_1$-$C_4$ alkyl radical;
$R_2$ is a methyl radical.

A second more particularly preferred family of compounds of formula (1) is that consisting of the 1,3,5-triazine derivatives described in document EP-A-0 570 838, which corresponds to the 1,3,5-triazines of formula (1) in which $A_1$, $A_2$ and $A_3$ are of formula (2) and have all of the following characteristics:
one or two $X_a$—$R_a$ represents the radical —NH—$R_a$ with $R_a$ chosen from: a linear or branched $C_1$-$C_{18}$ alkyl radical; a $C_5$-$C_{12}$ cycloalkyl radical optionally substituted with one or more $C_1$-$C_4$ alkyl radicals; a radical of formula (3), (4) or (5) above in which:
B' is a $C_1$-$C_4$ alkyl radical;
$R_2$ is a methyl radical;
the other or the other two $X_a$—$R_a$ being the radical —O—$R_a$ with $R_a$, which may be identical or different, chosen from: hydrogen; an alkali metal; an ammonium radical optionally substituted with one or more alkyl or hydroxyalkyl radicals; a linear or branched $C_1$-$C_{18}$ alkyl radical; a $C_5$-$C_{12}$ cycloalkyl radical optionally substituted with one or more $C_1$-$C_4$ alkyl radicals; a radical of formula (3), (4) or (5) above in which:
B' is a $C_1$-$C_4$ alkyl radical;
$R_2$ is a methyl radical.

A 1,3,5-triazine of formula (1) of this second family that is particularly preferred is 2-[(p-(tert-butylamido)anilino]-4,6-bis[(p-(2'-ethylhexyl-V-oxycarbonyl)anilino]-1,3,5-triazine or Diethylhexylbutamidotriazone sold under the trade name Uvasorb HEB by Sigma 3V and corresponding to the following formula:

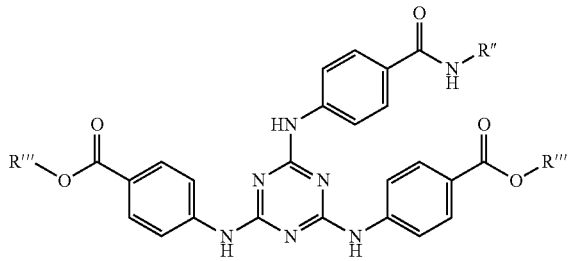

in which R''' denotes a 2-ethylhexyl radical and R'' denotes a tert-butyl radical.

A third preferred family of compounds of formula (1) that may be used in the context of the present invention, and which is especially described in document U.S. Pat. No. 4,724,137, which corresponds to the 1,3,5-triazines of formula (1) in which $A_1$, $A_2$ and $A_3$ are of formula (2) and have the following characteristics:

$X_a$ are identical and represent oxygen;

$R_a$, which may be identical or different, represent a $C_6$-$C_{12}$ alkyl radical or a polyoxyethylene radical comprising from 1 to 6 ethylene oxide units and in which the end OH group is methylated.

A 1,3,5-triazine of formula (1) of this third family that is particularly preferred is 2,4,6-tris[p-(2'-ethylhexyl-1'-oxycarbonyl)anilino]-1,3,5-triazine or Ethylhexyl triazone sold especially under the trade name Uvinul T 150 by the company BASF and corresponding to the following formula:

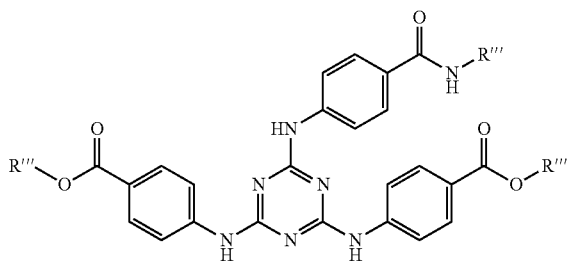

in which R''' denotes a 2-ethylhexyl radical.

(ii) the bis-resorcinyl-triazines of formula (6)

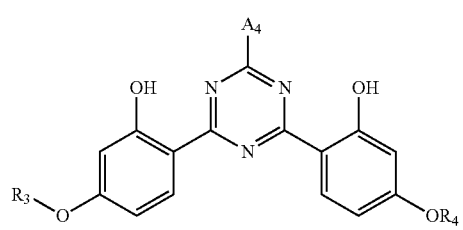

in which:
the radicals $R_3$ and $R_4$, which may be identical or different, denote a $C_3$-$C_{18}$ alkyl radical; a $C_2$-$C_{18}$ alkenyl radical or a residue of formula —CH$_2$—CH(OH)—CH$_2$—OT$_1$ in which T$_1$ is a hydrogen atom or a $C_1$-$C_8$ alkyl radical;

$A_4$ denotes a residue corresponding to one of the following formulae:

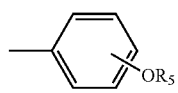
(7)

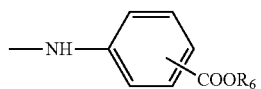
(8)

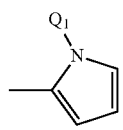
(9)

in which:
$R_5$ denotes a hydrogen atom, a $C_1$-$C_{10}$ alkyl radical, a radical of formula —(CH$_2$CHR$_7$—O)$_{n_1}$R$_6$ in which $n_1$ is a number from 1 to 16, or a residue of structure —CH$_2$—CH—(OH)—CH$_2$OT$_1$ with T$_1$ having the same meaning indicated above;

$R_6$ denotes hydrogen, a metal cation M, a $C_1$-$C_5$ alkyl radical or a residue of formula —(CH$_2$)$_{m_2}$-OT$_1$ in which $m_2$ is a number from 1 to 4 and T$_1$ has the same meaning indicated above;

$R_7$ is hydrogen or methyl, $Q_1$ is a $C_1$-$C_{18}$ alkyl radical.

The bis-resorcinyl triazine derivatives of formula (6) of the invention are screening agents that are already known per se. They are described and prepared according to the syntheses indicated in patent application EP-A-0 775 698.

As examples of compounds of formula (6) that may be used, mention may be made of:
2,4-bis{[4-(2-ethylhexyloxy)-2-hydroxy]phenyl}-6-(4-methoxyphenyl)-1,3,5-triazine;
2,4-bis{[4-(3-(2-propyloxy)-2-hydroxypropyloxy)-2-hydroxy]phenyl}-6-(4-methoxyphenyl)-1,3,5-triazine;
2,4-bis{[4-(2-ethylhexyloxy)-2-hydroxy]phenyl}-6-[4-(2-methoxyethylcarboxyl)phenylamino]-1,3,5-triazine;
1,3,5-triazine;
2,4-bis{[4-(2"-methylpropenyloxy)-2-hydroxy]phenyl}-6-(4-methoxyphenyl)-1,3,5-triazine;
2,4-bis{[4-(3-(2-propyloxy)-2-hydroxypropyloxy]-2-hydroxy]phenyl}-6-[(4-ethylcarboxyl)phenylamino]-1,3,5-triazine;
2,4-bis{[4-(2-ethylhexyloxy)-2-hydroxy]phenyl}-6-(1-methylpyrrol-2-yl)-1,3,5-triazine.

The compound derived from bis-resorcinyl triazine that is more particularly preferred according to the invention will be the compound 2,4-bis{[4-(2-ethylhexyloxy)-2-hydroxy]phenyl}-6-(4-methoxyphenyl)-1,3,5-triazine (INCI name: bis-Ethylhexyloxyphenol methoxyphenyl triazine sold under the trade name Tinosorb S by BASF.

(iii) the silicone triazines of formula (10) below or a tautomeric form thereof

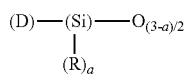
(10)

in which:

R, which may be identical or different, represent a linear or branched $C_1$-$C_{30}$ alkyl radical which is optionally halogenated or unsaturated, a $C_6$-$C_{12}$ aryl radical, a $C_1$-$C_{10}$ alkoxy radical, a hydroxyl radical or the trimethylsilyloxy group;

a=1 to 3; in addition to the units of formula -A-(Si)(R)$_a$(O)$_{(3-a)/2}$, the group (D) denotes an s-triazine compound of formula (11) below:

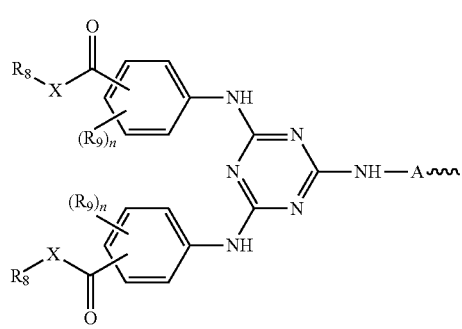

(11)

where

X represents —O— or —NR$_{10}$—, with R$_{10}$ representing hydrogen or a $C_1$-$C_5$ alkyl radical, R$_8$ represents a linear or branched $C_1$-$C_{30}$ alkyl radical which is optionally unsaturated and which may contain a silicon atom, a $C_5$-$C_{20}$ cycloalkyl group, optionally substituted with 1 to 3 linear or branched $C_1$-$C_4$ alkyl radicals, the group —(CH$_2$CHR$_{10}$—O)$_m$R$_{11}$ or the group —CH$_2$—CH(OH)—CH$_2$—O—R$_{12}$, R$_9$, which may be identical or different, represent a hydroxyl radical, a linear or branched $C_1$-$C_8$ alkyl radical or a $C_1$-$C_8$ alkoxy radical, it being possible for two adjacent R$_2$ groups on the same aromatic nucleus together to form an alkylidenedioxy group in which the alkylidene group contains 1 or 2 carbon atoms, R$_{10}$ represents hydrogen or methyl; it being possible for the group (C=O)XR$_8$ to be in the ortho, meta or para position relative to the amino group, R$_{11}$ represents hydrogen or a $C_1$-$C_8$ alkyl group, R$_{12}$ represents hydrogen or a $C_4$-$C_8$ alkyl group, m is an integer ranging from 2 to 20, n=0 to 2, A is a divalent radical chosen from methylene or a group corresponding to one of the formulae (12), (13), (14) or (15) below:

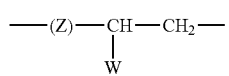

(12)

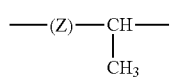

(13)

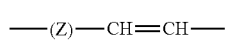

(14)

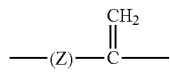

(15)

in which:

Z is a saturated or unsaturated, linear or branched $C_1$-$C_{10}$ alkylene diradical, optionally substituted with a hydroxyl radical or oxygen atoms and optionally containing an amino group, W represents a hydrogen atom, a hydroxyl radical or a saturated or unsaturated, linear or branched $C_1$-$C_8$ alkyl radical.

The organosiloxane may comprise units of formula: (R)$_b$—(Si)(O)$_{(4-b)/2}$ in which R has the same meaning as in formula (10), b=1, 2 or 3.

It should be noted that the derivatives of formula (10) can be used in their tautomeric forms and more particularly in the tautomeric form of formula (10') below:

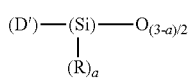

(10')

in which the group (D') denotes an s-triazine compound of formula (11') below:

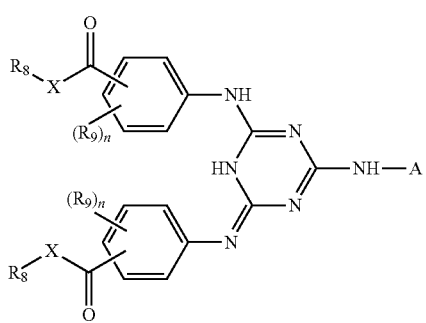

(11')

In addition to the units of formula -A-(Si)(R)$_a$(O)$_{(3-a)/2}$, the organosiloxane may comprise units of formula (R)$_b$—(Si)(O)$_{(4-b)/2}$ in which R has the same meaning as in formula (10), b=1, 2 or 3.

In formulae (10) and (10') as defined above, the alkyl radicals may be linear or branched, saturated or unsaturated and chosen especially from methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The alkyl radical that is particularly preferred is the methyl radical.

The preferential s-triazine derivatives are those for which, in formula (10) or (10'), at least one and even more preferentially all of the following characteristics are satisfied:

R is methyl, a=1 or 2,

R$_8$ is a $C_2$-$C_8$ radical,

Z=—CH$_2$—,

W=H.

Preferably, the s-triazine compounds of formula (10) of the invention are represented by formulae (10a), (10b) and (10c) below:

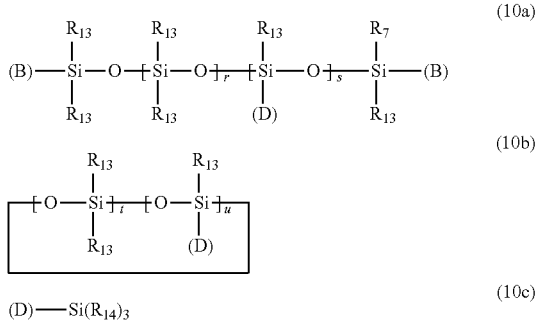

in which:
(D) corresponds to formula (11) as defined above,
R$_{13}$, which may be identical or different, are chosen from linear or branched C$_1$-C$_{20}$ alkyl, phenyl, 3,3,3-trifluoropropyl and trimethylsilyloxy radicals or the hydroxyl radical,
R$_{14}$, which may be identical or different, are chosen from linear or branched C$_1$-C$_{20}$ alkyl and alkenyl radicals, hydroxyl radicals or phenyl radicals,
(B), which may be identical or different, are chosen from the R$_{13}$ radicals and the (D) radical,
r is an integer between 0 and 200 inclusive,
s is an integer ranging from 0 to 50 and, if s=0, at least one of the two (B) symbols denotes (D),
u is an integer ranging from 1 to 10,
t is an integer ranging from 0 to 10, it being understood that t+u is equal to or greater than 3, and the tautomeric forms thereof.

The linear diorganosiloxanes of formula (10a) are particularly preferred.

The linear or cyclic diorganosiloxanes of formula (10a) or (10b) falling within the scope of the present invention are random oligomers or polymers preferably having at least one and even more preferentially all of the following characteristics:

R$_{13}$ is a methyl radical, a C$_1$-C$_2$ alkoxy radical or a hydroxyl radical,
B is preferentially methyl (in the case of the linear compounds of formula (10a)).

As examples of particularly preferred compounds of formula (10), mention will be made of the compounds of formulae (10$_1$) to (10$_{14}$) below, and the tautomeric forms thereof:

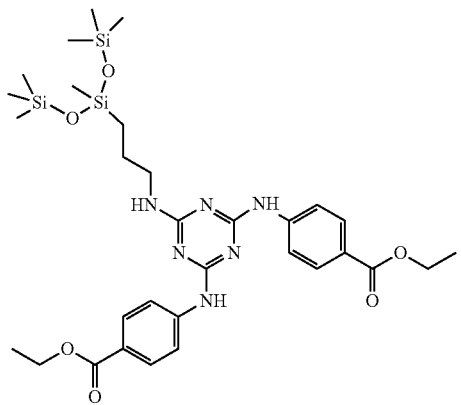

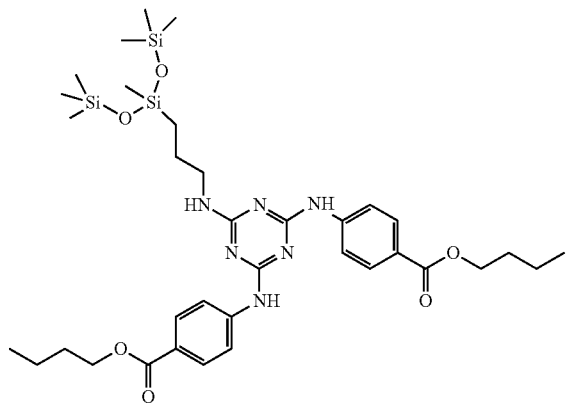

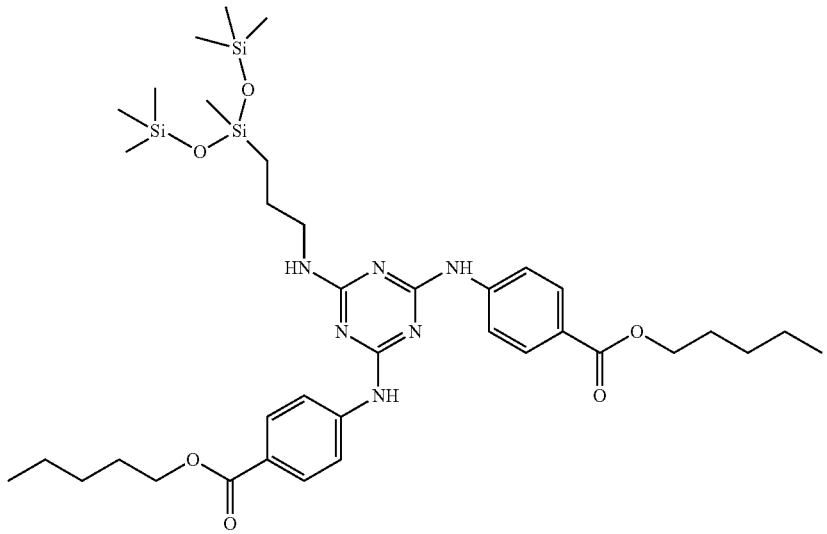

(10₄)
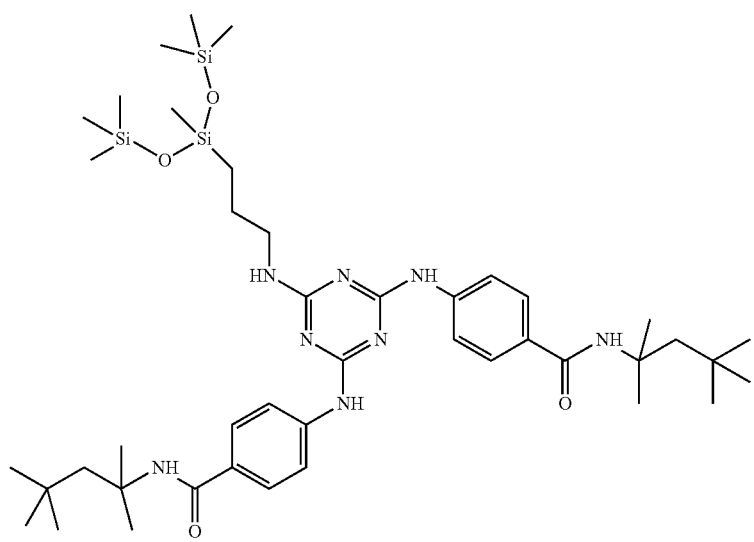
(10₅)
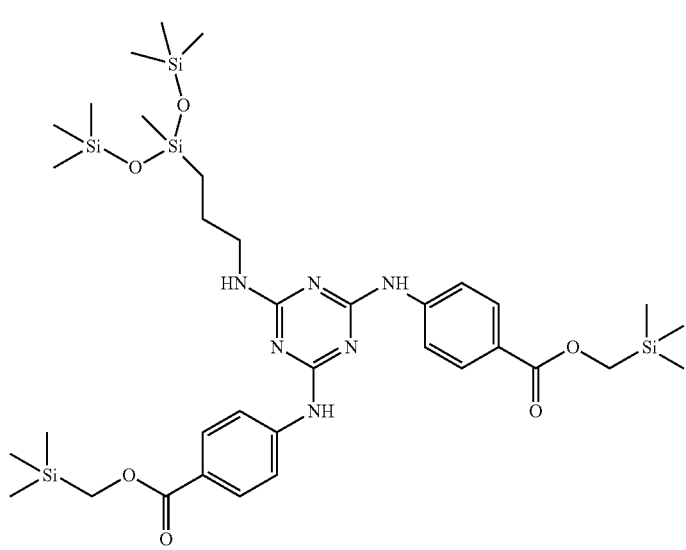
(10₆)
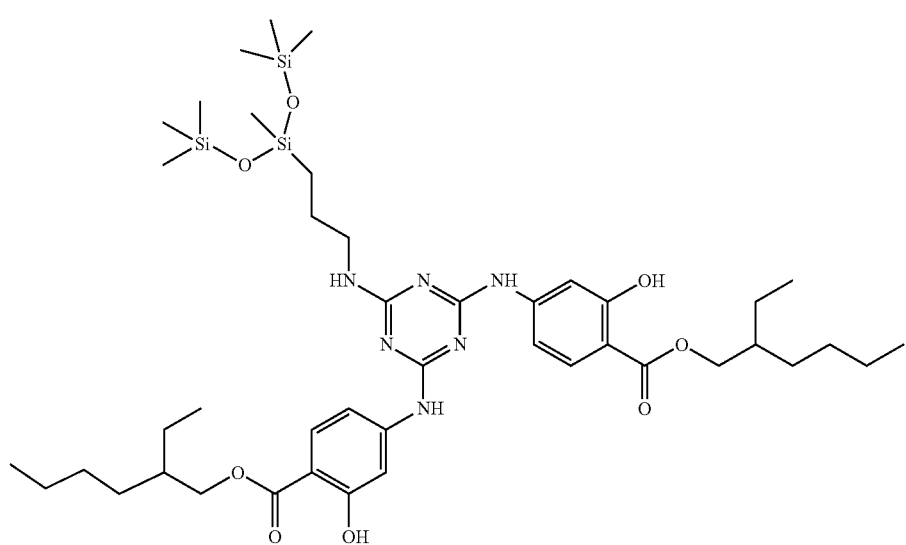

(10₇)
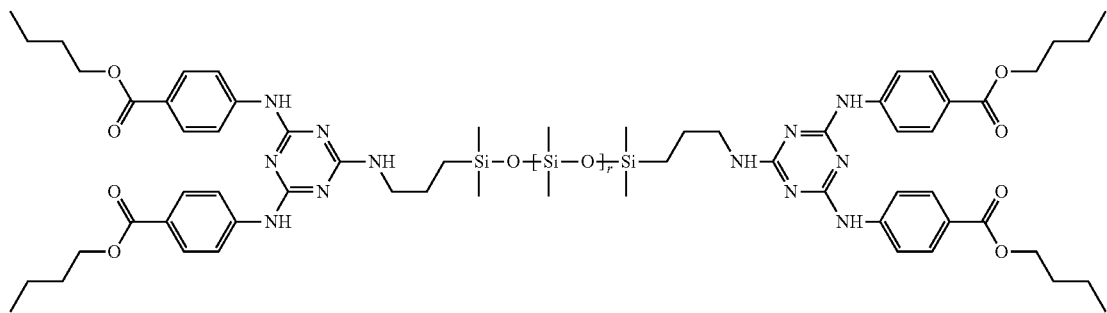
with r = 8,
(10₈)                    (10₉)
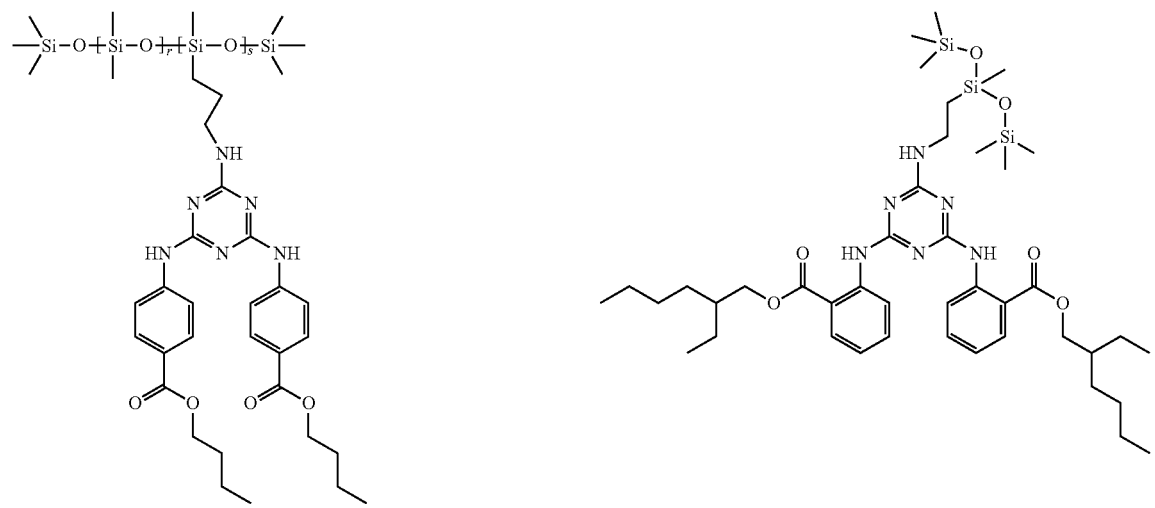
(10₁₀)
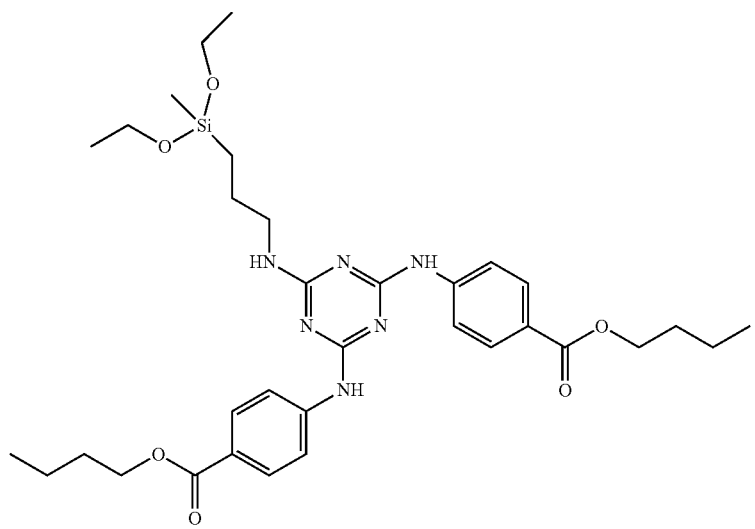

-continued
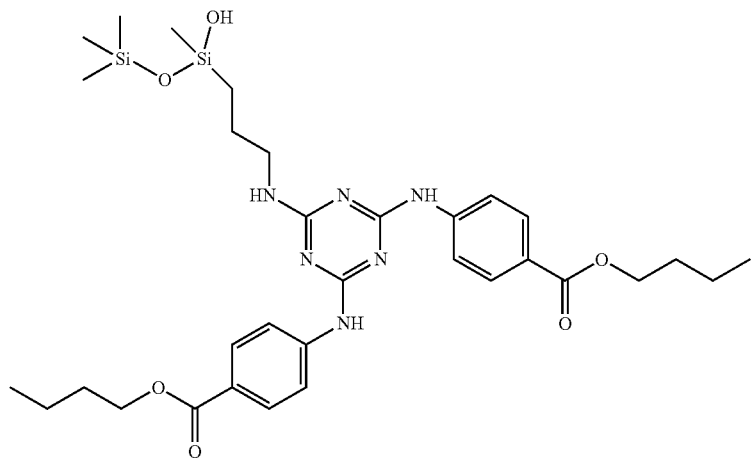
(10₁₁)
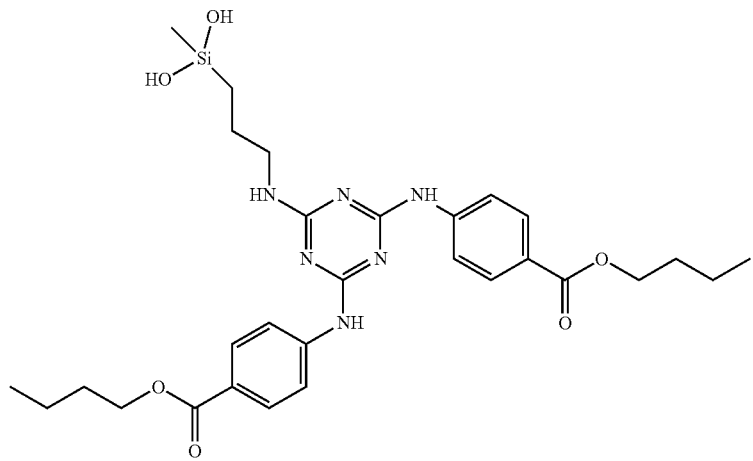
(10₁₂)
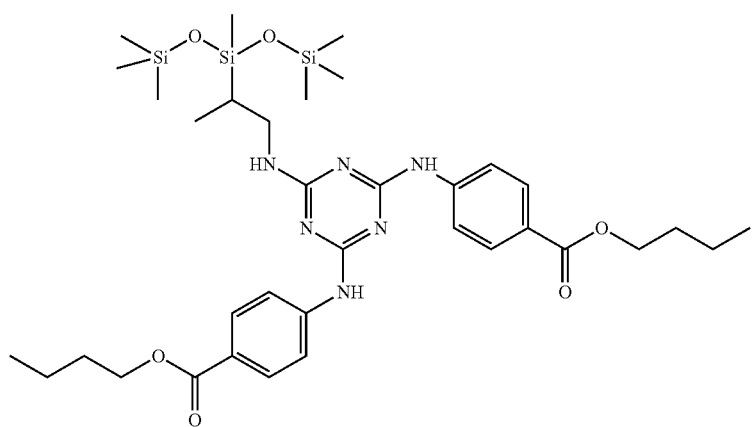
(10₁₃)

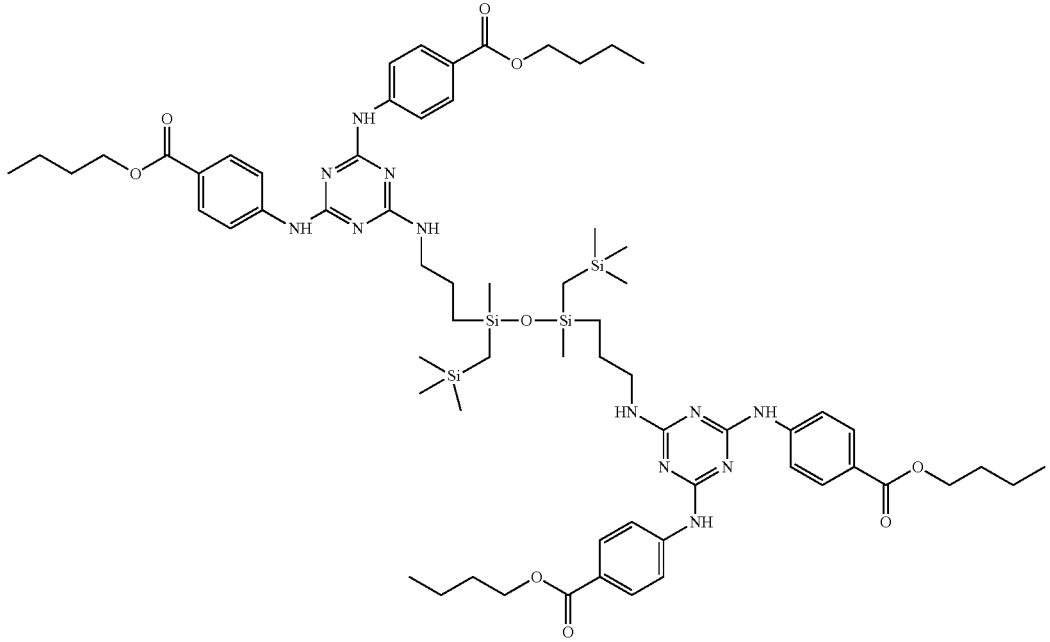

(10₁₄)

Use will be made more particularly of the compound 2,4-bis(n-butyl 4'-diylaminobenzoate)-6-{[1,3,3,3-tetramethyl-1-[(trimethylsilyl)oxy]disiloxanyl]propyl-3-ylamino}-s-triazine of structure (10₂):

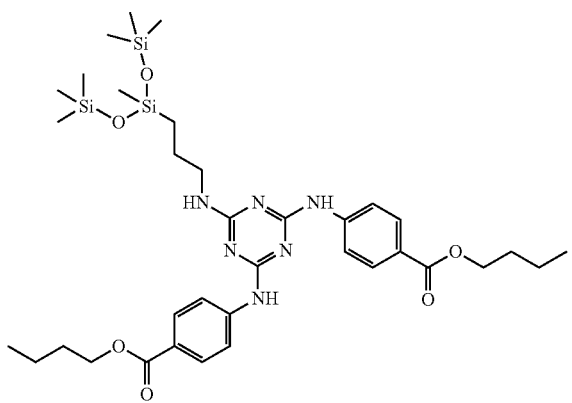

(10₂)

The triazines of formula (10) and the synthesis thereof were described in patent application EP 1 891 079.

Among the water-insoluble solid UV-screening agents of the triazine type that are particularly preferred according to the invention, mention may be made especially of:

Bis-ethylhexylphenol methoxyphenyl triazine sold under the trade name Tinosorb S by BASF, Diethylhexylbutamidotriazone sold under the trade name Uvasorb HEB by Sigma 3V, 2,4-Bis(n-butyl 4'-aminobenzoate)-6-[(3-{1,3,3,3-tetramethyl-1-[(trimethylsilyl)oxy]disiloxanyl}propyl)amino]-s-triazine, 2,4,6-tris[p-(2'-ethylhexyl-1'-oxycarbonyl)anilino]-1,3,5-triazine or Ethylhexyl triazone sold especially under the trade name Uvinul T 150 by the company BASF, and mixtures thereof.

Water-Insoluble Solid UV-Screening Agents (A) of the Benzophenone Type

Among the water-insoluble solid UV-screening agents of the benzophenone type according to the invention, mention may be made especially of:

Benzophenone-1 sold under the trade name Uvinul 400 by BASF,

Benzophenone-2 sold under the trade name Uvinul D50 by BASF,

Benzophenone-3 or Oxybenzone sold under the trade name Uvinul M40 by BASF,

Benzophenone-5

Benzophenone-6 sold under the trade name Helisorb 11 by Norquay,

Benzophenone-8 sold under the trade name Spectra-Sorb UV-24 by American Cyanamid, Benzophenone-12 n-Hexyl 2-(4-diethylamino-2-hydroxybenzoyl)benzoate sold under the trade name Uvinul A+.

Water-Insoluble Solid UV-Screening Agents (A) of the Merocyanine Type

Among the water-insoluble solid UV-screening agents of the merocyanine type, according to the invention, mention may be made of those mentioned in patent applications WO 04/006 878, WO 05/058 269 and WO 06/032 741, especially the compound octyl 5-N,N-diethylamino-2-phenysulfonyl-2,4-pentadienoate.

Mention may also be made of those described in patent application WO 2011/113 719, in particular the water-insoluble solid merocyanine dicyano or cyanoacetate derivatives according to the invention:

(i) those corresponding to the general formula (16) below:

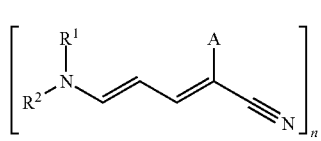
(16)

in which:
- A is the —C≡N or —(C=O)OR³ group,
- R¹ and R², which may be identical or different, denote a linear or branched $C_1$-$C_3$ alkyl radical or a $C_5$-$C_6$ cycloalkyl,
- R³ denotes a linear or branched $C_1$-$C_8$ alkyl radical,
- n is 1 or 2;

with the proviso that, when n=2, R¹, R² or R³ is a $C_2$-$C_{16}$ alkyl diradical or else $R_1$ and $R_2$ form, with 2 nitrogen atoms, a cyclic divalent —$(CH_2)_m$— radical with m being an integer ranging from 3 to 7;

(ii) compound (a):

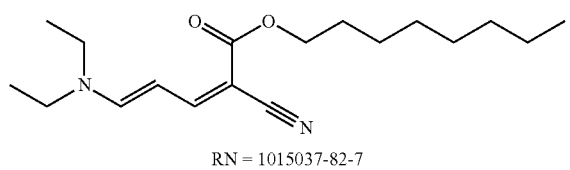
(a)

RN = 1015037-82-7

(iii) compound (b):

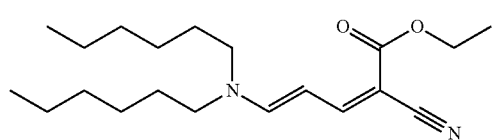
(b)

RN = 193292-32-9

(iv) compound (c):

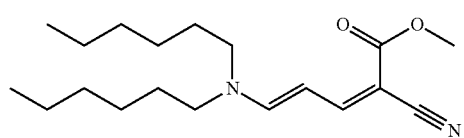
(c)

RN = 105596-16-5

(v) compound (I):

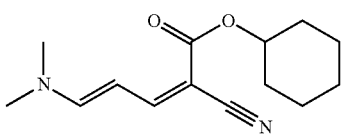
(I)

(vi) compound (aa)

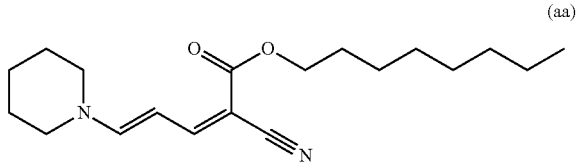 [SMILES: CCCCCCCCOC(=O)/C(C#N)=C\C=C\N1CCCCC1]
(aa)

(vii) compound (bb)

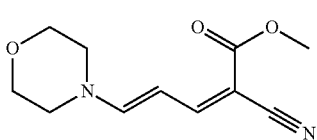
(bb)

RN = 467465-33-4

The compounds of formula (16) and compounds (a), (b), (c), (I), (aa) and (bb) can be in the E,E-, E,Z- or Z,Z- geometrical isomer forms.

When n=2, the term "diradical" means a divalent radical such that the two units

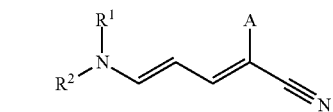

are bonded to each other via this diradical.

By way of illustration, mention may be made of compound (q) below:

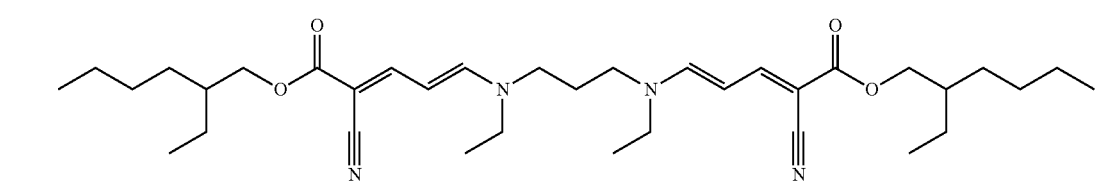
(q)

RN = 647829-03-6

Examples of linear or branched $C_1$-$C_3$ alkyl radicals that may be mentioned include: methyl, ethyl, n-propyl, 1-methylethyl, isopropyl.

Among the compounds of formula (16), mention may be made of those of formulae (e), (f), (g), (h), (i), (j), (q), (cc) and (ee) below, or the E,E-, E,Z- or Z,Z-isomers thereof:

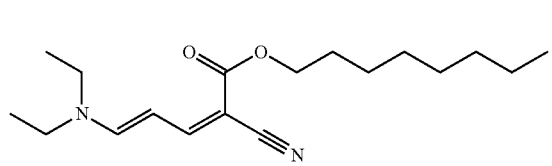
(e)

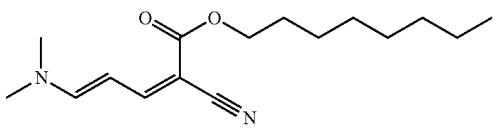
(f)

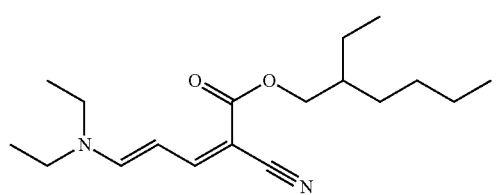
(g)
RN = 647829-00-3

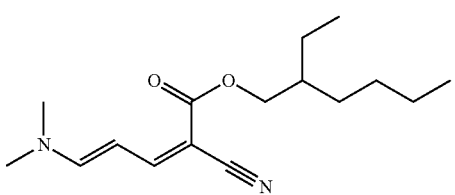
(h)
RN = 256444-60-7

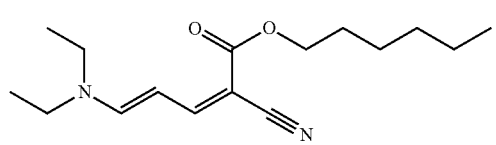
(i)

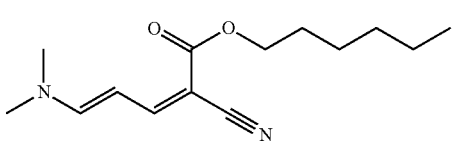
(j)

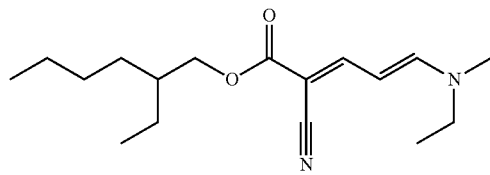
(q)
RN = 647829-03-6

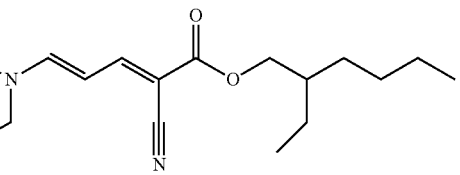
(cc)

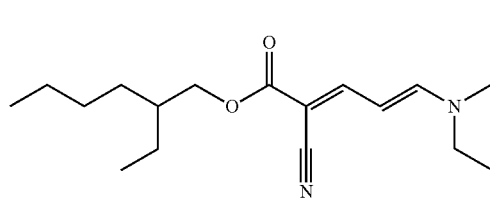
RN = 647829-05-8

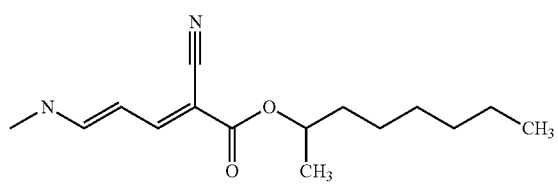
(ee)

Examples of linear or branched $C_1$-$C_8$ alkyl radicals that may be mentioned include: methyl, ethyl, n-propyl, 1-methylethyl, isopropyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl.

$C_5$-$C_6$ cycloalkyl radicals that may be mentioned include cyclopentyl and cyclohexyl.

Water-Insoluble Solid UV-Screening Agents (A) of the Benzylidenecamphor Type

Among the UV-screening agents of the benzylidenecamphor type according to the invention, mention may be made of:

3-Benzylidenecamphor manufactured under the name Mexoryl SD by Chimex,

4-Methylbenzylidenecamphor, sold under the name Eusolex 6300 by Merck or sold under the trade name Parsol 5000 by the company DSM Nutritional Products or Neo Heliopan MBC by the company Symrise.

Water-Insoluble Solid UV-Screening Agents (A) of the Phenylbenzotriazole Type

Among the water-insoluble solid UV-screening agents of the phenylbenzotriazole type according to the invention, mention may be made of silanes or polyorganosiloxanes bearing a benzotriazole function as described in patent applications EP-A-0 392 883; EP-A-0 660 701; EP-A-0 708 108; EP-A-0 711 778; EP-A-711 779 and especially comprising at least one unit of formula (17) below:

   (17)

in which:
R$^4$ represents an optionally halogenated C$_1$-C$_{10}$ alkyl radical or a phenyl radical or a trimethylsilyloxy radical, a' is an integer chosen between 0 and 3 inclusive, and the symbol G' denotes a monovalent radical linked directly to a silicon atom, and which corresponds to formula (18) below:

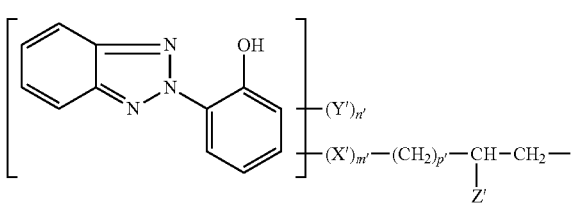   (18)

in which:
radicals Y', which may be identical or different, are chosen from C$_1$-C$_8$ alkyl radicals, halogens and C$_1$-C$_4$ alkoxy radicals, it being understood that, in the latter case, two adjacent radicals Y' on the same aromatic nucleus can together form an alkylidenedioxy group in which the alkylidene group contains from 1 to 2 carbon atoms, X' represents O or NH, Z' represents hydrogen or a C$_1$-C$_4$ alkyl radical, n' is an integer between 0 and 3 inclusive, m' is 0 or 1, p' represents an integer between 1 and 10 inclusive.

These compounds are described especially in patent applications EP-A-0 392 883; EP-A-0 660 701; EP-A-0 708 108; EP-A-0 711 778; EP-A-711 779.

Preferably, the siliceous derivatives used in the context of the present invention belong to the general family of silicone benzotriazoles that is described especially in EP-A-0 660 701.

A family of silicone benzotriazoles that is particularly suitable for performing the present invention is that combining the compounds corresponding to formula (19) or (20) below:

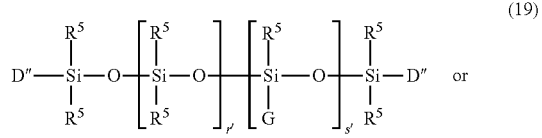   (19)

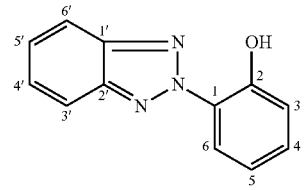   (20)

in which:
R$^5$, which may be identical or different, are chosen from C$_1$-C$_{10}$ alkyl, phenyl, 3,3,3-trifluoropropyl and trimethylsilyloxy radicals, at least 80% by number of the radicals R$^5$ being methyl, D'', which may be identical or different, are chosen from the R$^5$ radicals and the radical G', r' is an integer between 0 and 50 inclusive, and s' is an integer between 0 and 20 inclusive, and if s'=0, at least one of the two symbols D'' denotes G', u' is an integer between 1 and 6 inclusive, and t' is an integer between 0 and 10 inclusive, it being understood that t'+u' is greater than or equal to 3, and the symbol G' denotes a monovalent radical linked directly to a silicon atom, and which corresponds to formula (18) as defined previously.

As emerges from formula (18) given above, the attachment of the chain unit —(X)$_{m'}$—(CH$_2$)$_{p'}$—CH(Z')—CH$_2$— to the benzotriazole unit, which thus provides the connection of the said benzotriazole unit to the silicon atom of the silicone chain, may, according to the present invention, take place in any of the available positions offered by the two aromatic nuclei of the benzotriazole:

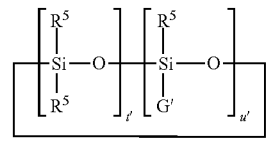

Preferably, this attachment takes place in position 3, 4 or 5 (aromatic nucleus bearing the hydroxyl function) or 4' (benzene nucleus adjacent to the triazole ring), and even more preferentially in position 3, 4 or 5. In a preferred embodiment of the invention, the attachment takes place in position 3.

Similarly, the attachment of the substituent unit(s) Y' may take place in any of the other available positions in the benzotriazole. However, preferably, this attachment takes place in position 3, 4, 4', 5 and/or 6. In a preferred embodiment of the invention, the attachment of the unit Y' takes place in position 5.

In formulae (19) and (20) above, the alkyl radicals may be linear or branched and chosen especially from methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals R$^5$ according to the invention are methyl, ethyl, propyl, n-butyl, n-octyl and 2-ethylhexyl radicals. Even more preferentially, the radicals R$^5$ are all methyl radicals.

Among the compounds of formula (19) or (20) above, it is preferred to use those corresponding to formula (19), i.e. diorganosiloxanes with a short linear chain.

Among the compounds of formula (19) above, it is preferred to use those for which the radicals D" are both radicals $R^5$.

Among the linear diorganosiloxanes of formula (19) falling within the context of the present invention, random derivatives or well-defined derivatives in blocks having at least one and even more preferentially all of the characteristics below are more particularly preferred:

D" is a radical $R^5$, $R^5$ is alkyl and even more preferentially methyl, r' is between 0 and 15 inclusive; s' is between 1 and 10 inclusive, n' is non-zero, and preferably equal to 1, and Y' is then chosen from methyl, tert-butyl and $C_1$-$C_4$ alkoxy, Z' is hydrogen or methyl, m'=0, or [m'=1 and X'=O]— p' is equal to 1.

A family of silicone benzotriazoles that is particularly suitable for the invention is that defined by the general formula (21) below:

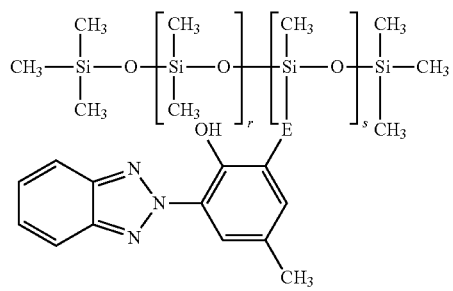

with
$0 \leq r \leq 10$,
$1 \leq s \leq 10$, and in which E represents the divalent radical:

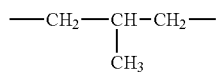

Processes that are suitable for preparing the products of formulae (17), (19), (20) and (21) above are described especially in American patents U.S. Pat. Nos. 3,220,972, 3,697,473, 4,340,709, 4,316,033 and 4,328,346 and in patent applications EP-A-0 392 883 and EP-A-0 742 003.

In a particularly preferred embodiment of the invention, the water-insoluble solid UV-screening agent of the phenyl-benzotriazole type is the compound Drometrizole trisiloxane sold under the name Silatrizole by Rhodia Chimie, corresponding to the following formula:

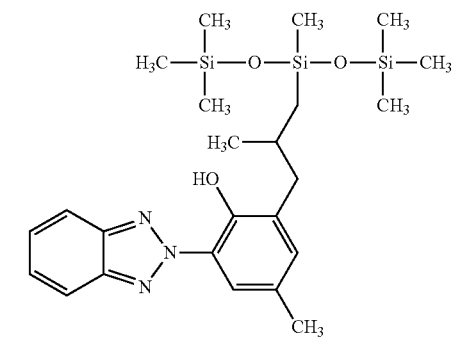 [SMILES: Cc1cc(CC(C)C[Si](C)(O[Si](C)(C)C)O[Si](C)(C)C)c(O)c(-n2nc3ccccc3n2)c1]

Water-Insoluble Solid UV-Screening Agents (A) of the Para-Aminobenzoic Type

Among the UV-screening agents of the para-aminobenzoic type according to the invention, mention may be made of:

Ethyl dihydroxypropyl PABA,

Ethylhexyl dimethyl PABA sold in particular under the name Escalol 507 by ISP.

The water-insoluble solid organic UV-screening agent(s) are preferably present in the compositions according to the invention in proportions ranging from 0.01% to 20% by weight, relative to the total weight of the composition, and preferably ranging from 0.1% to 10% by weight, relative to the total weight of the composition.

Galenical Forms

The compositions according to the invention may be in any common acceptable form for a cosmetic composition. They may thus be in the form of a suspension or a dispersion, in particular of oil in water by means of vesicles; an optionally thickened or even gelled organic or oily solution; an oil-in-water, water-in-oil or multiple emulsion; a gel or a mousse; an oily or emulsified gel; a dispersion of vesicles, in particular lipid vesicles; a two-phase or multiphase lotion; a spray; a lotion, a cream, a salve, a soft paste, an ointment, a solid that has been cast or moulded in particular as a stick or in a dish, or a compacted solid.

Those skilled in the art may select the appropriate galenical form, and also the method for preparing it, on the basis of their general knowledge, taking into account firstly the nature of the constituents used, in particular their solubility in the support, and secondly the intended application of the composition.

According to a particular form of the invention, the compositions according to the invention are in the form of an oil-in-water or water-in-oil emulsion.

The emulsification processes that may be used are of the paddle or impeller, rotor-stator and HPH type.

It is also possible, by means of an HPH (between 50 and 800 bar), to obtain stable dispersions with droplet sizes that may be as low as 100 nm.

The emulsions generally contain at least one emulsifying surfactant chosen from amphoteric, anionic, cationic and nonionic emulsifying surfactants, which are used alone or as a mixture. The emulsifiers are appropriately chosen according to the emulsion to be obtained (W/O or O/W).

As emulsifying surfactants that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, sold under the name DC 5225 C by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R by the company Goldschmidt, and the mixture of cetyldimethicone copolyol, of polyglyceryl isostearate (4 mol) and of hexyl laurate, sold under the name Abil WE O9 by the company Goldschmidt. One or more coemulsifiers may also be added thereto, which may be chosen advantageously from the group comprising polyol alkyl esters.

Polyol alkyl esters that may especially be mentioned include polyethylene glycol esters, for instance PEG-30 dipolyhydroxystearate, such as the product sold under the name Arlacel P135 by the company ICI.

Glycerol and/or sorbitan esters that may be mentioned include, for example, polyglyceryl isostearate, such as the product sold under the name Isolan GI 34 by the company Goldschmidt; sorbitan isostearate, such as the product sold under the name Arlacel 987 by the company ICI; sorbitan glyceryl isostearate, such as the product sold under the name Arlacel 986 by the company ICI, and mixtures thereof.

For the O/W emulsions, examples of emulsifying surfactants that may be mentioned include nonionic emulsifying surfactants such as oxyalkylenated (more so particularly polyoxyethylenated) esters of fatty acids and of glycerol; oxyalkylenated esters of fatty acids and of sorbitan; oxyalkylenated (oxyethylenated and/or oxypropylenated) esters of fatty acids, such as the PEG 100 stearate/glyceryl stearate mixture sold, for example, by the company ICI under the name Arlacel 165; oxyalkylenated (oxyethylenated and/or oxypropylenated) ethers of fatty alcohols; esters of sugars, such as sucrose stearate; or ethers of fatty alcohol and of sugar, in particular alkyl polyglucosides (APGs), such as decyl glucoside and lauryl glucoside, sold, for example, by the company Henkel under the respective names Plantaren 2000 and Plantaren 1200, cetostearyl glucoside, optionally as a mixture with cetostearyl alcohol, sold, for example, under the name Montanov 68 by the company SEPPIC, under the name Tegocare CG90 by the company Goldschmidt and under the name Emulgade KE3302 by the company Henkel, and also arachidyl glucoside, for example in the form of a mixture of arachidyl alcohol, behenyl alcohol and arachidyl glucoside, sold under the name Montanov 202 by the company SEPPIC. According to a particular embodiment of the invention, the mixture of the alkylpolyglucoside as defined above with the corresponding fatty alcohol may be in the form of a self-emulsifying composition, for example as described in document WO-A-92/06778.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The compositions according to the invention in the form of vaporizable fluid lotions in accordance with the invention may be applied to the skin or the hair in the form of fine particles by means of pressurization devices. The devices in accordance with the invention are well known to those skilled in the art and comprise non-aerosol pumps or "atomizers", aerosol containers comprising a propellant and aerosol pumps using compressed air as propellant. These devices are described in patents U.S. Pat. Nos. 4,077,441 and 4,850,517 (which form an integral part of the content of the description).

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

The compositions in accordance with the invention have improved gloss and improved persistence of the said gloss when compared with the prior art, and may be used for caring for or making up keratin materials such as the skin, the eyelashes, the eyebrows, the nails or the lips, and more particularly for making up the lips, the eyelashes and/or the face.

They may thus be in the form of a product for caring for and/or making up bodily or facial skin, the lips, the eyelashes, the eyebrows or the nails; an antisun or self-tanning product; they are advantageously in the form of a makeup composition, especially a mascara, an eyeliner, a lipstick, a lip gloss, a makeup so rouge, an eyeshadow, a foundation, a nail varnish or a nailcare product.

A subject of the invention is also a cosmetic process for treating keratin materials, especially bodily or facial skin, the lips, the nails and/or the eyelashes, comprising the application to the said materials of a cosmetic composition as defined previously.

This process according to the invention especially allows the care or makeup of the said keratin materials, in particular of the lips and/or the nails, by applying a composition, especially a lipstick, a lip gloss, a nailcare product or a nail varnish according to the invention.

Additives

According to a particular form of the invention, the compositions in accordance with the invention may comprise, in addition to compounds (A) and (B), at least one volatile or non-volatile hydrocarbon-based oil and/or one volatile and/or non-volatile silicone oil.

For the purposes of the invention, the term "volatile oil" means an oil that is capable of evaporating on contact with the keratin materials in less than one hour, at room temperature and atmospheric pressure. The volatile oil(s) of the invention are volatile cosmetic oils, which are liquid at room temperature, having a non-zero vapour pressure, at room temperature and atmospheric pressure, in particular ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on keratin materials, at room temperature and atmospheric pressure, for at least several hours and that especially has a vapour pressure of less than 10-3 mmHg (0.13 Pa).

The composition according to the invention may also comprise at least one wax of plant, animal, mineral or synthetic origin, or even a silicone wax.

The compositions in accordance with the present invention may also comprise one or more standard cosmetic adjuvants chosen from softeners, humectants, opacifiers, stabilizers, emollients, fragrances, preserving agents, cosmetic or dermatological active agents, polymers, fillers, a colouring agent or any other ingredient usually used in cosmetics and/or dermatology.

Needless to say, a person skilled in the art will take care to select the abovementioned optional additional compound(s) and/or the amounts thereof such that the advantageous properties intrinsically associated with the compositions in accordance with the invention are not, or are not substantially, adversely affected by the envisaged addition(s).

Among the cosmetic or dermatological active agents, mention may be made of:
- vitamins and derivatives or precursors thereof, alone or as mixtures;
- antioxidants;
- free-radical scavengers;
- water-soluble UV-screening agents;
- mineral UV-screening agents;
- self-tanning agents;
- antiglycation agents;
- calmatives;
- NO-synthase inhibitors;
- agents for stimulating the synthesis of dermal or epidermal macromolecules and/or for preventing their degradation;
- agents for stimulating fibroblast proliferation;
- agents for stimulating keratinocyte proliferation;
- dermorelaxants;
- tensioning agents;
- matting agents;
- keratolytic agents;
- desquamating agents;
- moisturizers;
- anti-inflammatory agents;
- agents that act on the energy metabolism of cells;
- insect repellents;
- substance P or CGRP antagonists;
- anti-wrinkle agents;
- agents for preventing light-induced ageing.

Needless to say, a person skilled in the art will take care to select the optional additional screening agent(s) and/or the amounts thereof such that the advantageous properties intrinsically associated with the compositions in accordance with the invention are not, or are not substantially, adversely affected by the envisaged addition(s).

According to a particular form, the compositions of the invention also comprise one or more fillers of organic or mineral nature which especially give it additional improved sensory, matting, covering, persistence and/or stability properties.

The term "filler" should be understood as meaning colourless or white, solid particles of any form, which are in a form that is insoluble and dispersed in the medium of the composition. These particles, of mineral or organic nature, can give body or rigidity to the composition and/or softness and uniformity to the makeup.

The fillers used in the compositions according to the present invention may be in lamellar, globular or spherical form, in the form of fibres or in any other intermediate form between these defined forms.

The fillers according to the invention may or may not be surface-coated, and in particular they may be surface-treated with silicones, amino acids, fluoro derivatives or any other substance that promotes the dispersion and compatibility of the filler in the composition.

Colouring Agent

The colouring agent, if it is present in the compositions of the invention, is chosen, for example, from the group consisting of pigments, dyes and interference particles.

According to one embodiment, the colouring agent is chosen from pigments.

A cosmetic composition in accordance with the invention may advantageously incorporate at least one colouring agent chosen from organic or mineral dyestuffs, especially such as the pigments or nacres conventionally used in cosmetic compositions, liposoluble or water-soluble dyes, materials with a specific optical effect, and mixtures thereof.

The term "pigments" should be understood as meaning white or coloured, mineral or organic particles that are insoluble in the medium of the composition, which are intended to colour and/or opacify the resulting film.

The term "nacres" should be understood as meaning iridescent or non-iridescent coloured particles of any form, especially produced by certain molluscs in their shell, or else synthesized, and which have a colour effect by optical interference.

The cosmetic composition according to the invention may also comprise water-soluble or fat-soluble dyes.

A person skilled in the art will choose the said active agent(s) as a function of the effect desired on the keratin materials.

According to a particular form of the invention, the composition is thus in the form of a skin and/or lip makeup composition, especially for facial or bodily skin; it may be a complexion product such as a foundation, a makeup rouge or an eyeshadow; a lip product such as a lipstick; a gloss (lip gloss) or a lipcare product; a concealer product; a blusher; an eyeliner; a lip pencil or an eye pencil; a body makeup product.

According to a particularly preferred form, the composition will be a lip product such as a lipstick; a gloss (lip gloss) or a lipcare product.

Assembly

According to another aspect, the invention also relates to a cosmetic assembly comprising:

i) a container delimiting one or more compartment(s), the said container being closed by a closing member and optionally not being leaktight; and ii) a makeup and/or care composition in accordance with the invention placed inside the said compartment(s).

The container will preferably be in the form of a jar.

The closing member can be in the form of a lid comprising a cap mounted so as to be able to move by translation or by pivoting relative to the container housing the said makeup and/or care composition(s).

The examples which follow serve to illustrate the invention without, however, exhibiting a limiting nature. In these examples, the amounts of the composition ingredients are given as weight percentages relative to the total weight of the composition.

EXAMPLES

Synthesis Examples

Compounds (B1) and (B2) below of the invention were used.

Synthesis of Compound (B1): 2-Decyltetradecanol Functionalized with Ureidopyrimidone

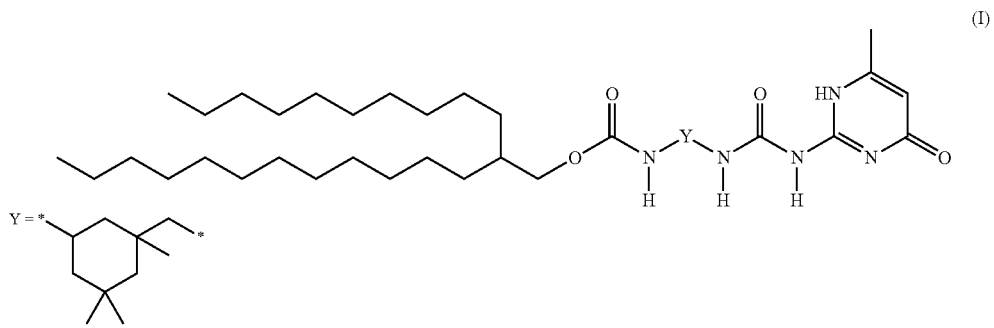

(I)

126 g of 2-decyltetradecanol (Jarcol I-24®, JARCHEM, CAS #[58670-89-6]) were heated at 100° C. under reduced pressure for 4 hours to dry them. Next, the oil thus dried was added, over 4 hours, at 50° C. and under argon, to a mixture of 94.7 g of isophorone diisocyanate (IPDI, CAS #[4098-71-9]) and of dibutyltin dilaurate catalyst (DBTDL, CAS #[77-58-7]). Assay of the isocyanate allowed the reaction progress to be monitored. At half-equivalence, 126 g of propylene carbonate (PC, CAS #[108-32-7]) and 53.3 g of 6-methylisocytosine (MIC, CAS #[3977-29-5]) were added. Stirring and heating were continued at 100° C. for 16 hours, and disappearance of the isocyanate was monitored by infrared spectroscopy. Disappearance of the peak at 2250 $cm^{-1}$ was observed. In parallel, the disappearance of the amine originating from the isocytosine was monitored by means of an amine assay. At the end of the reaction, the temperature was reduced to 50° C., 100 ml of ethanol were added and stirring was continued for 5 hours. After filtering through Celite and stripping with isododecane, the desired product conveyed in isododecane, at a solids content of 50%, was obtained. The product was especially characterized by GPC and HPLC coupled to mass spectroscopy.

Synthetic scheme for compound (B1)

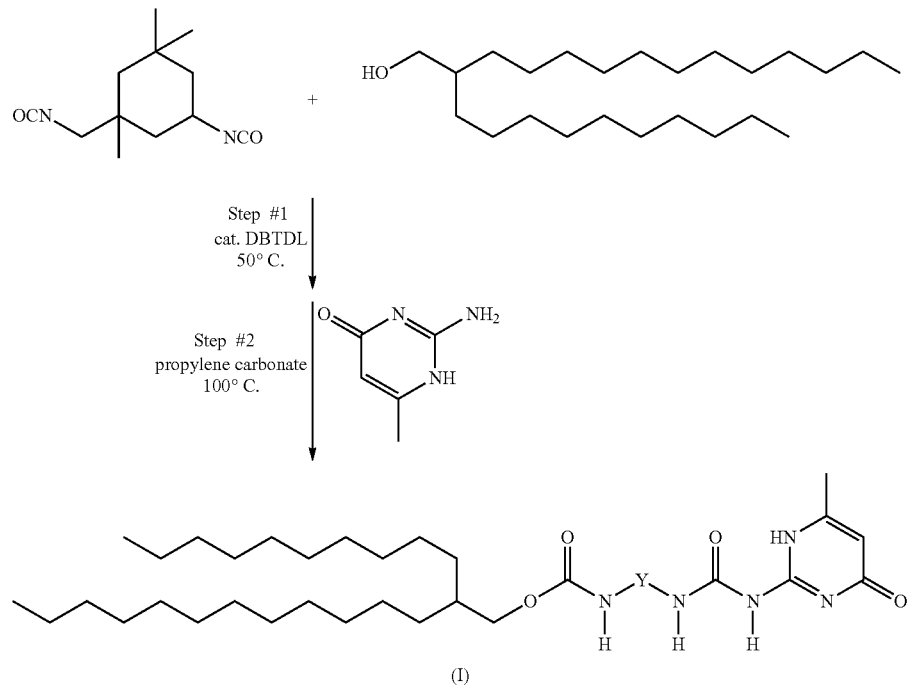

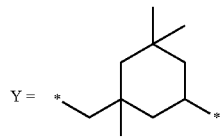

Synthesis of Compound (B2): Diisostearyl Malate Functionalized with a Ureidopyrimidone

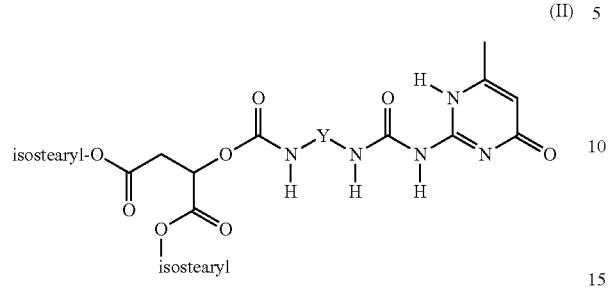

(II)

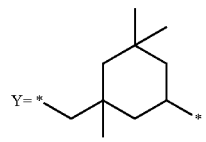

The same process as for the preparation of (B1) was used, replacing the Jarcol I-24® with diisostearyl malate (CAS #[67763-18-2], Lubrizol). The desired product conveyed in isododecane, in a solids content of 50%, was obtained. The product was especially characterized by GPC and HPLC coupled to mass spectroscopy.

The Following Water-Insoluble Solid Organic UV-Screening Agents (A) were Used:

UV-screening agent No. 1 of the dibenzoylmethane type: Butylmethoxydibenzoylmethane (Parsol 1789®)

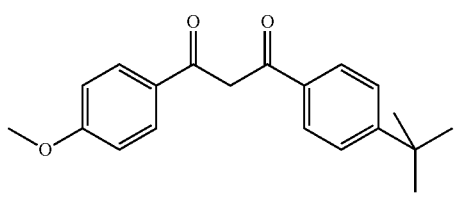 [SMILES: COc1ccc(C(=O)CC(=O)c2ccc(C(C)(C)C)cc2)cc1]

UV-screening agent No. 2 of the phenylbenzotriazole type (Drometrizole Trisiloxane®):

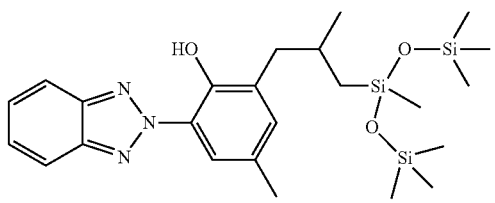 [SMILES: Cc1cc(CC(C)C[Si](C)(O[Si](C)(C)C)O[Si](C)(C)C)c(O)c(-n2nc3ccccc3n2)c1]

UV-screening agent No. 3 of the merocyanine type:

Synthetic scheme for compound (B2)

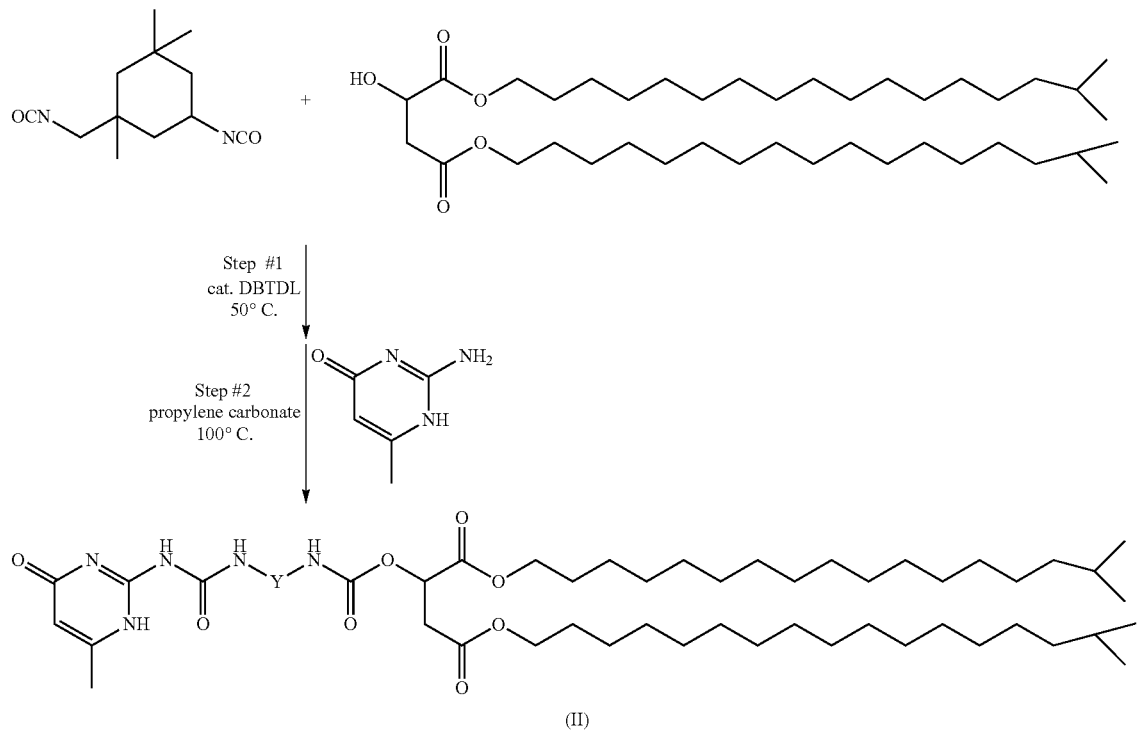

+ other products (u)

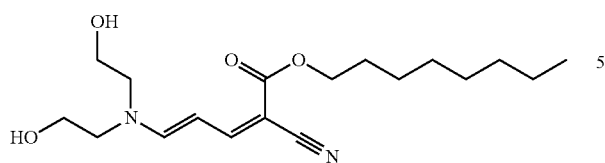

UV-screening agent No. 4 of the merocyanine type:

(e)

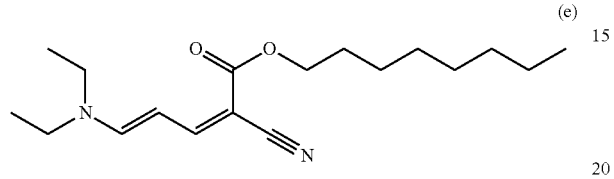

UV-screening agent No. 5 of the triazine type: Ethylhexyl triazone (Uvinul T150®)

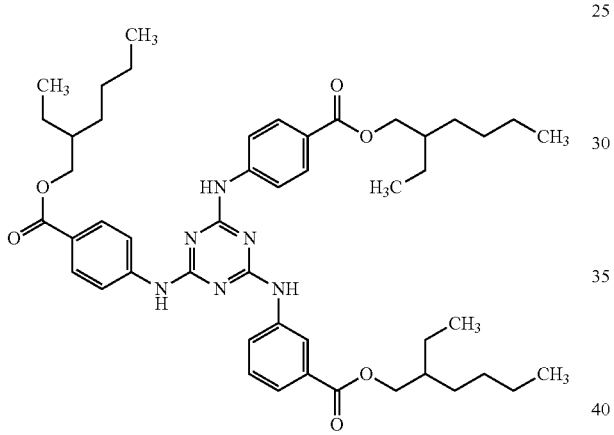

UV-screening agent No. 6 of the triazine type: 2,4-bis(n-butyl 4'-aminobenzoate)-6-[(3-{1,3,3,3-tetramethyl-1-[(trimethylsilyl)oxy]-disiloxanyl}propyl)amino]-s-triazine,

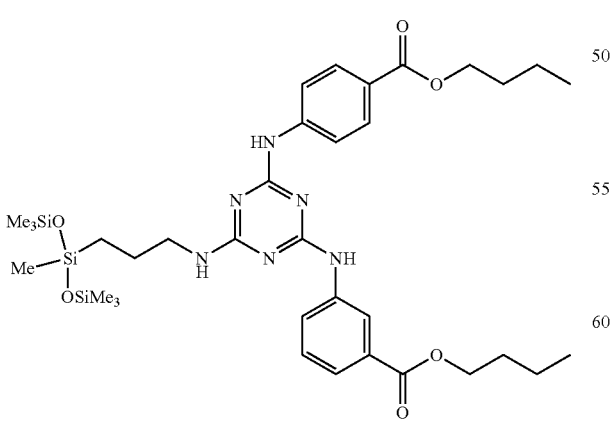

The synthesis of this screening agent is described in patent FR 96/13684.

UV-screening agent No. 7 (outside the invention): n-butyl 4-[(4,6-bis{[4-(butoxycarbonyl)phenyl]amino}-1,3,5-triazin-2-yl)amino]benzoate)triazine:

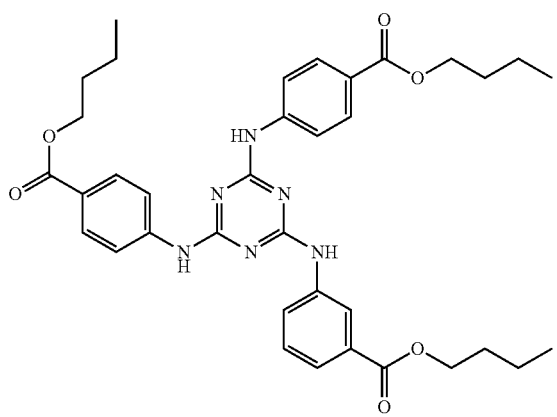 [SMILES: CCCCOC(=O)c1ccc(Nc2nc(Nc3ccc(C(=O)OCCCC)cc3)nc(Nc3cccc(C(=O)OCCCC)c3)n2)cc1]

UV-screening agent No. 8 of the triazine type: 2,4-bis{[4-(2-ethylhexyloxy)-2-hydroxy]phenyl}-6-(4-methoxyphenyl)-1,3,5-triazine (INCI name: bis-Ethylhexyloxyphenol methoxyphenyl triazine sold under the trade name Tinosorb S by BASF.

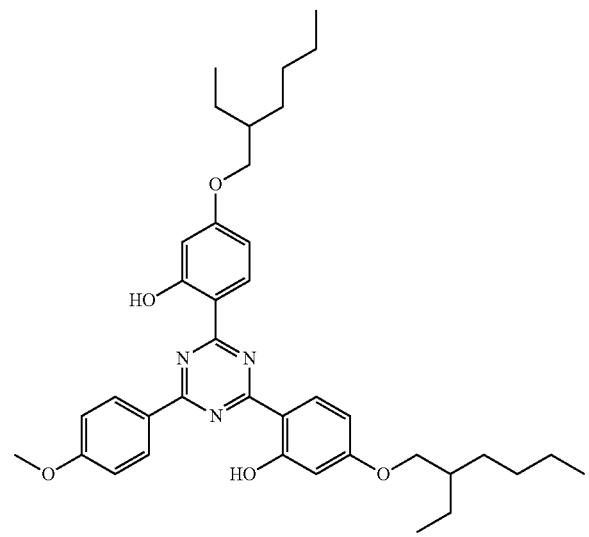 [SMILES: CCCCC(CC)COc1ccc(-c2nc(-c3ccc(OC)cc3)nc(-c3ccc(OCC(CC)CCCC)cc3O)n2)c(O)c1]

Solubility Test of the Screening Agents (A) in Mixtures of Compounds (B) and of Isododecane —

Maximum Solubility:

300 mg of water-insoluble solid UV-screening agent (A) or of UV-screening agent outside the invention were weighed out in a 10 ml flask, and compound (B) (as a mixture at 50% by weight in isododecane) was then added in increasing amounts until dissolution of the screening agent was complete. The dissolution was performed by sonication at 45° C. for 30 minutes, followed by cooling to room temperature. The stability of the solution was checked over two months at room temperature; the solution was considered stable when no formation of precipitate was observed at the end of this period. The maximum solubility was given in w/w %, which represents the mass percentage of UV-screening agent in the (B)/isododecane/UV-screening agent mixture. The maximum solubility of the solid screening agent (A) in a solution of isododecane alone (Bo) was also measured as reference. The results are as follows:

| UV-screening agent | Compound (B) | Maximum solubility of the UV-screening agent (w/w %) |
|---|---|---|
| UV-screening agent No. 1 - Butylmethoxydibenzoylmethane (invention) | (B$_0$) | 1 |
| | (B1) | 15 |
| | (B2) | 15 |
| UV-screening agent No. 2 - Drometrizole trisiloxane (invention) | (B$_0$) | 5 |
| | (B1) | 30 |
| | (B2) | 30 |
| UV-screening agent No. 3 of the merocyanine type (invention) | (B$_0$) | insoluble |
| | (B1) | 5 |
| | (B2) | 2.5 |
| UV-screening agent No. 4 - merocyanine type (invention) | (B$_0$) | insoluble |
| | (B1) | 2.5 |
| | (B2) | 5 |
| UV-screening agent No. 5: Ethylhexyl triazone (Uvinul T150 ®) (invention) | (B$_0$) | <1 |
| | (B1) | 20 |
| | (B2) | 20 |
| UV-screening agent No. 6 - 2,4-bis(n-butyl 4'-aminobenzoate)-6-[(3-{1,3,3,3-tetramethyl-1-[(trimethylsilyl)oxy]disiloxanyl}propyl)amino]-s-triazine (invention) | (B$_0$) | <3 |
| | (B1) | 10 |
| | (B2) | 10 |
| UV-screening agent No. 7 n-butyl 4-[(4,6-bis{[4-(butoxycarbonyl)phenyl]amino}-1,3,5-triazin-2-yl)amino]benzoate)triazine (outside the invention) | (B$_0$) | insoluble |
| | (B1) | insoluble |
| | (B2) | insoluble |
| UV-screening agent No. 8 bis-Ethylhexyloxyphenol methoxyphenyl triazine (Tinosorb S ®) (invention) | (B$_0$) | 1 |
| | (B1) | 5 |
| | (B2) | 5 |

These results show that compounds B1 and B2 make it possible to dissolve screening agents (A) Nos. 1 to 6 and 8.

Gloss Tests of Films Containing Water-Insoluble Solid UV-Screening Agents (A) in Compounds (B)

Preparation of the Films:

The UV-screening agent/isododecane/compound (B) mixtures as prepared previously were diluted by adding the 50/50 weight/weight compound (B)/isododecane mixture such that the concentration of UV-screening agent is at 2.5% or 5% by weight in the isododecane/compound (B) mixture, and the mixture was then heated at 45° C. for 30 minutes, followed by cooling to room temperature to obtain a homogeneous mixture. The films were prepared on contrast cards, using a 100 µm film spreader, and dried (drying, i.e. removal of the isododecane by evaporation at room temperature at atmospheric pressure) for 24 hours at room temperature. Films based on a 50/50 weight/weight compound (B)/isododecane mixture, without UV-screening agent (A), were also prepared, in the same manner, to serve as controls in the gloss measurement. Isododecane does not participate in the gloss of the film. As a result of its volatility, it disappears at the time of the gloss measurement.

Gloss Measurement:

The gloss of the films prepared previously was measured with a glossmeter (Dr Lange Ref 03 Reflektometer glossmeter) at three angles (20, 60 and 85°); the reported values are average values (minimum of two measurements) at 20° for the films prepared at the indicated w/w % values.

| UV-screening agent | Compound (B) | Concentration of UV-screening agent as a weight percentage in the isododecane/compound (B) mixture | Gloss of the film obtained |
|---|---|---|---|
| Reference without screening agent | (B1) | 0 | 69 ± 1 |
| | (B2) | 0 | 72 ± 1 |
| UV-screening agent No. 1 - Butylmethoxydibenzoylmethane (invention) | (B1) | 5 | 74 ± 1 |
| | (B2) | 5 | 77 ± 1 |
| UV-screening agent No. 2 - Drometrizole trisiloxane (invention) | (B1) | 5 | 81 ± 1 |
| | (B2) | 5 | 81 ± 1 |
| UV-screening agent No. 3 of the merocyanine type (invention) | (B1) | 2.5 | 79 ± 1 |
| | (B2) | 2.5 | 81 ± 1 |
| UV-screening agent No. 4 - merocyanine type (invention) | (B1) | 2.5 | 83 ± 1 |
| | (B2) | 5 | 83 ± 1 |
| UV-screening agent No. 5: Ethylhexyl triazone (Uvinul T150 ®) (invention) | (B1) | 5 | 84 ± 1 |
| | (B2) | 5 | 84 ± 1 |
| UV-screening agent No. 6 - 2,4-bis(n-butyl 4'-aminobenzoate)-6-[(3-{1,3,3,3-tetramethyl-1-[(trimethylsilyl)oxy]disiloxanyl}propyl)amino]-s-triazine (invention) | (B1) | 5 | 82 ± 1 |
| | (B2) | 5 | 82 ± 1 |

-continued

| UV-screening agent | Compound (B) | Concentration of UV-screening agent as a weight percentage in the isododecane/compound (B) mixture | Gloss of the film obtained |
|---|---|---|---|
| UV-screening agent No. 7 n-butyl 4-[(4,6-bis{[4-(butoxycarbonyl)phenyl]amino}-1,3,5-triazin-2-yl)amino]benzoate)triazine (outside the invention) | (B1) (B2) | insoluble insoluble | N/A N/A |
| UV-screening agent No. 8 bis-Ethylhexyloxyphenol methoxyphenyl triazine (Tinosorb S ®) (invention) | (B1) (B2) | 5 5 | 84 ± 1 83 ± 1 |

On account of its insolubility, the films containing the UV-screening agent No. 7 (outside the invention) could not be prepared.

It was observed, firstly, that compounds (B) made it possible to dissolve the screening agents (A) in accordance with the invention in the 50/50 weight/weight compound (B)/isododecane mixture and, secondly, that compounds (B) formed with the said screening agents (A) a homogeneous film with enhanced gloss relative to the film obtained without UV-screening agent.

Examples 1 and 2 of Lipsticks

The following lipsticks were prepared

| Constituents | Ingredient | Example 1 (invention) | Example 2 (outside the invention) |
|---|---|---|---|
| a) | Compound (B1) at a solids content of 11% in isododecane | 20% | 20% |
| b) | Phenyl trimethicone | 40% | 45% |
| c) | UV-screening agent No. 2 - Drometrizole trisiloxane (Mexoryl XL) | 5% | — |
| d) | Performalene 500-L Polyethylene | 15% | 15% |
| e) | Phenyl trimethicone/Red 7 (3/1) | 20% | 20% |

Preparation Process

The mass ratios of the components are detailed in the table; the mixtures were prepared so as to have 150 g of final mixture.

Components a), b) and c) were mixed using a Rayneri blender at 100° C. until homogeneous (~5 minutes).

Next, component d) was added and the mixture thus obtained was stirred at 100° C. until homogeneous (~5 minutes).

Next, component e) was added and the mixture thus obtained was stirred at 100° C. until homogeneous (~20 minutes).

The mixture was transferred into a lipstick mould heated to 42° C., and the assembly was then allowed to cool to room temperature, before being cooled to 4° C. for 20 minutes, and then opened.

The lipstick wands thus obtained were placed in hermetically sealed packaging to prevent evaporation of the isododecane.

Evaluation of the Gloss

The two lipsticks of Examples 1 and 2 were evaluated on the hand in a blind test by a panel of 10 experts. 10 out of 10 people judged the film formed on the hand with Example 1 of the invention to be glossier than the film formed using Example 2 on the hand.

The invention claimed is:

1. A composition comprising, in a cosmetically acceptable medium, a) a water-insoluble solid organic UV-screening agent (A) having a solubility in water of less than 0.1% at 25° C. and at an atmospheric pressure of 760 mmHg and having a solubility of at least 1% in isopropyl N-lauroyl sarcosinate, at 25° C. and at an atmospheric pressure of 760 mmHg selected from the group consisting of Butylmethoxydibenzoylmethane, compound having the following formula:

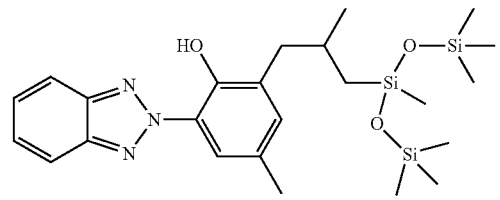

and Ethylhexyl triazone, and b) at least one a compound (B) selected from the group consisting of B 1: 2-Decyltetradecanol functionalized with ureidopyrimidone having the following formula:

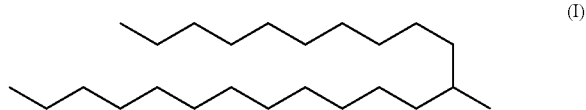

(I)

-continued

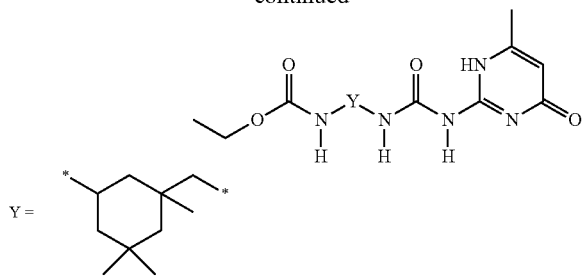

and B2: Diisostearyl malate functionalized with a ureidopyrimidone having the following formula:

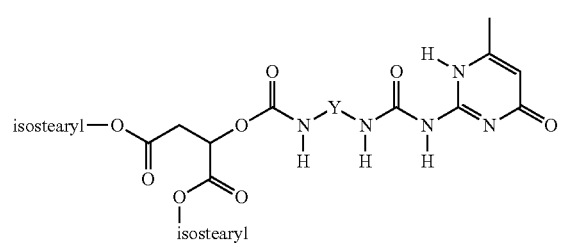

(II)

-continued and c) at least one volatile or non-volatile hydrocarbon-based oil and/or at least one volatile or non-volatile silicon-based oil.

2. The composition according to claim 1, in which the amount of compound (B) present in the compositions ranges between 1% and 80% by weight.

3. The composition according to claim 1, wherein the water-insoluble solid organic UV-screening agent (A) is Butylmethoxydibenzoylmethane.

4. The composition according to claim 3, wherein the B compound has the following formula:

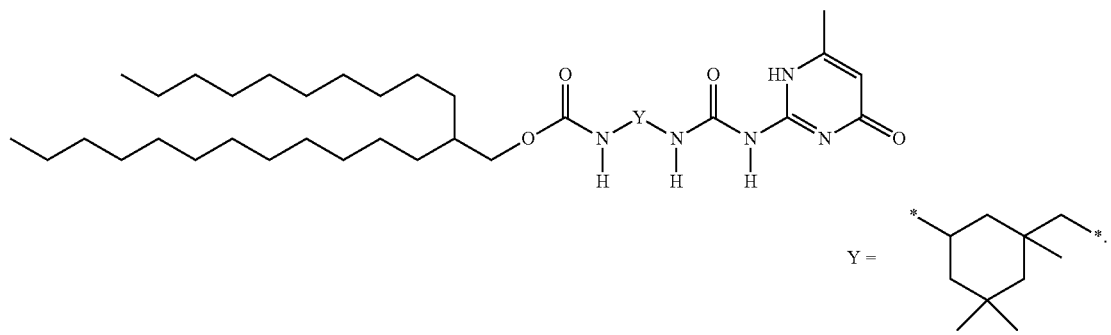

(I)

5. The composition according to claim 3, wherein the B compound has the following formula:

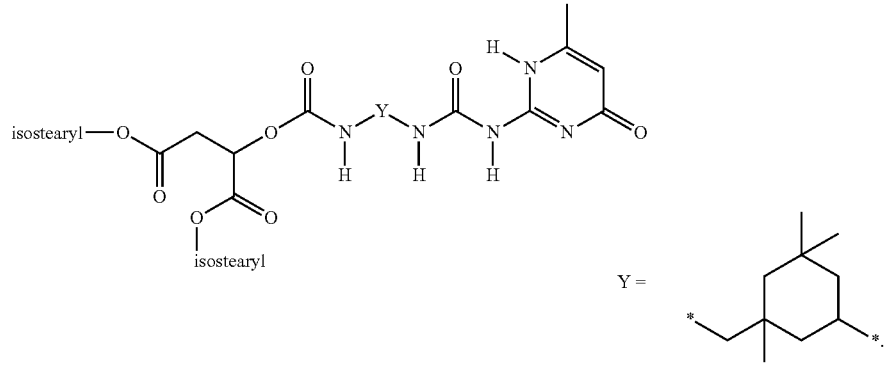

(II)

6. The composition according to claim 1, wherein the B compound has the following formula:

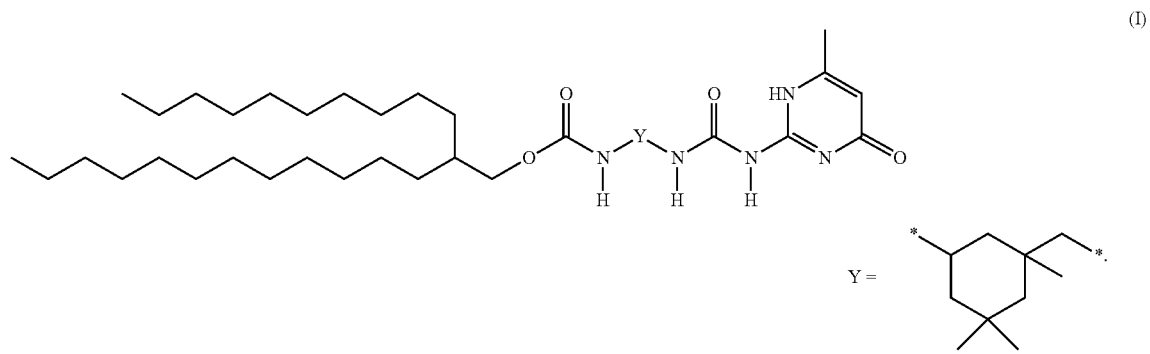

7. The composition according to claim 1, wherein the B compound has the following formula:

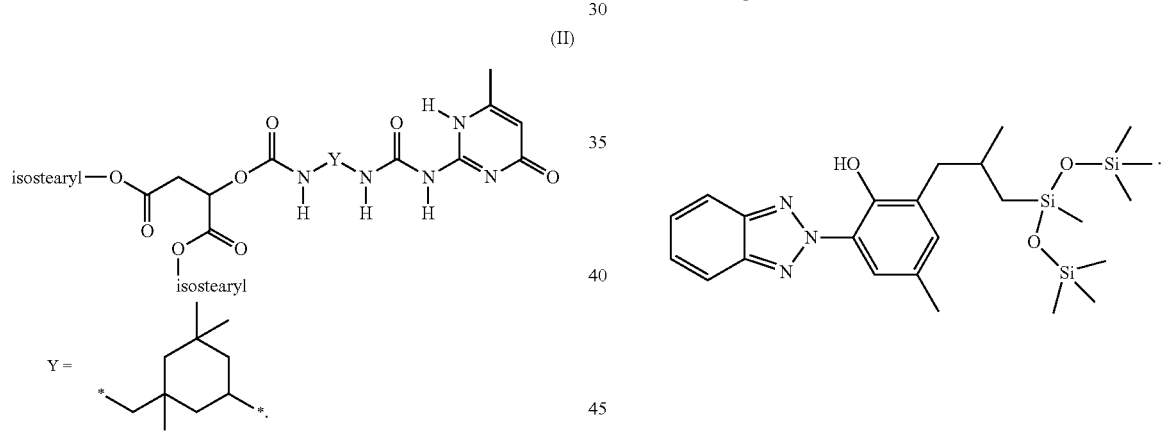

8. The composition according to claim 1, wherein the water-insoluble solid organic UV-screening agent (A) has the following formula:

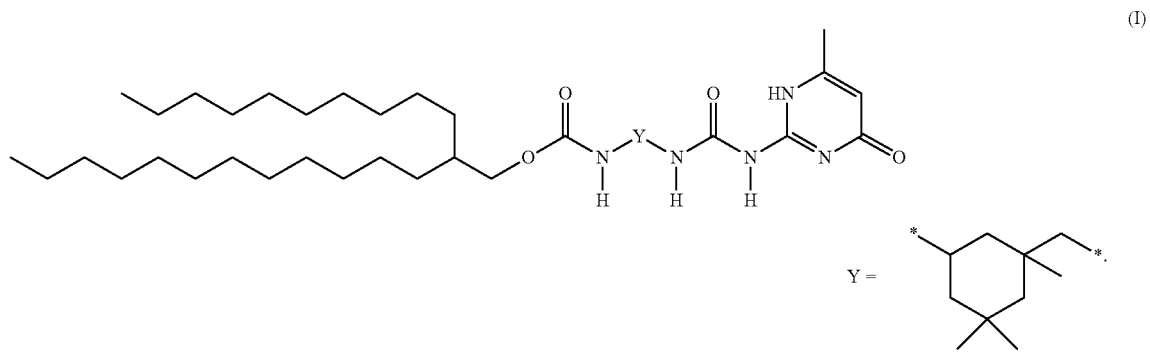

9. The composition according to claim 8, wherein the B compound has the following formula:

10. The composition according to claim 8, wherein the B compound has the following formula:

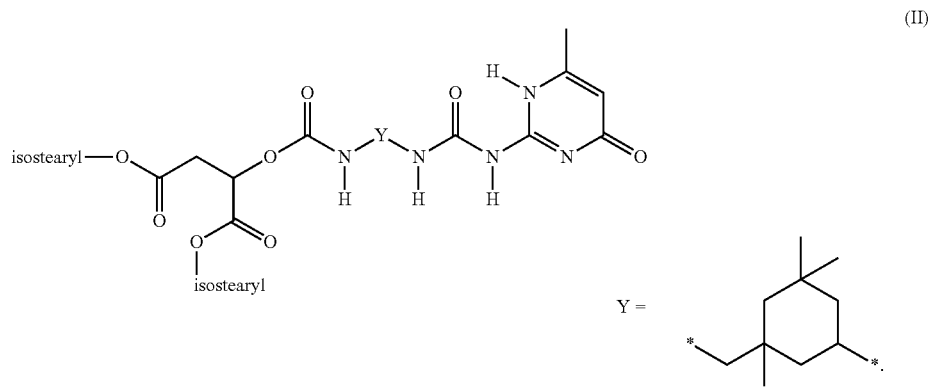

(II)

11. The composition according to claim 1, wherein the water-insoluble solid organic UV-screening agent (A) is Ethylhexyl triazone.

12. The composition according to claim 11, wherein the B compound has the following formula:

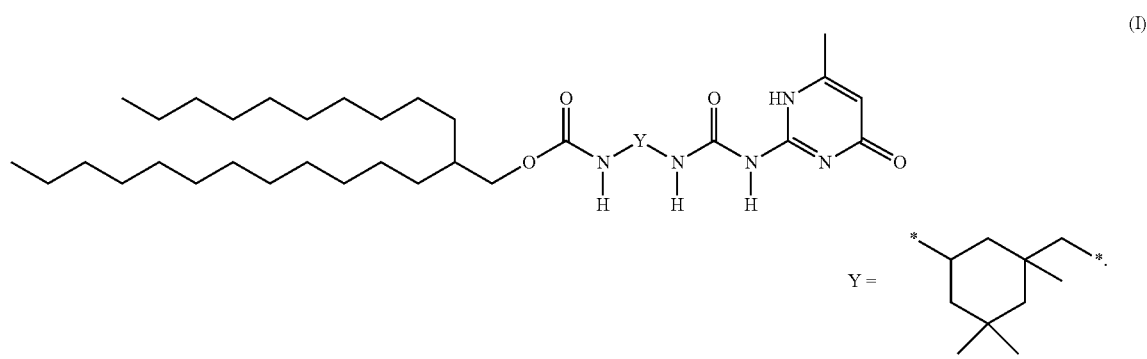

(I)

13. The composition according to claim 11, wherein the B compound has the following formula:

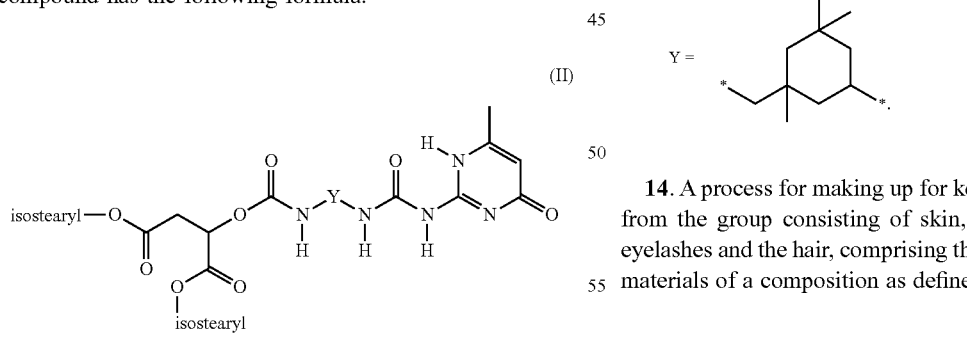

(II)

14. A process for making up for keratin materials selected from the group consisting of skin, the lips, the nails, the eyelashes and the hair, comprising the application to the said materials of a composition as defined according to claim 1.

* * * * *